(12) United States Patent (10) Patent No.: US 8,770,338 B1
Duncan et al. (45) Date of Patent: Jul. 8, 2014

(54) EARPIECES, SYSTEMS, AND METHODS

(71) Applicant: Syzygy Memory Plastics, Dallas, TX (US)

(72) Inventors: Phillip Brent Duncan, Lewisville, TX (US); Michael Robert Moussa, Euless, TX (US); James C. Amato, Dallas, TX (US)

(73) Assignee: Syzygy Memory Plastics, Dallas, TX (US)

( * ) Notice: Subject to any disclaimer, the term of this patent is extended or adjusted under 35 U.S.C. 154(b) by 0 days.

(21) Appl. No.: 13/838,759

(22) Filed: Mar. 15, 2013

Related U.S. Application Data

(63) Continuation-in-part of application No. 29/446,576, filed on Feb. 25, 2013.

(51) Int. Cl.
*A61B 7/02* (2006.01)
(52) U.S. Cl.
USPC ........................................... 181/135; 181/130
(58) Field of Classification Search
USPC ................................................ 181/130, 135
See application file for complete search history.

(56) References Cited

U.S. PATENT DOCUMENTS 8,299,191 B2   10/2012   Voit et al.

FOREIGN PATENT DOCUMENTS

WO   2013/116811 A1   8/2013

OTHER PUBLICATIONS

U.S. Appl. No. 61/594,508, filed Feb. 3, 2012, 61 pages.

*Primary Examiner* — Forrest M Phillips
(74) *Attorney, Agent, or Firm* — Baker & McKenzie LLP

(57) ABSTRACT

The present disclosure relates, according to some embodiments, to devices, systems, and methods for modifying received and/or perceived sound. For example, a device for altering sound received at a subject's ear may comprise an elongated earpiece having a proximal portion and a distal portion and defining a longitudinal axis (e.g., together defining a longitudinal axis). A proximal portion may comprise an insert configured for at least partial insertion in the canal of the subject's ear. A distal end may comprise a handle configured to guide insertion of the insert in the subject's ear canal.

23 Claims, 28 Drawing Sheets

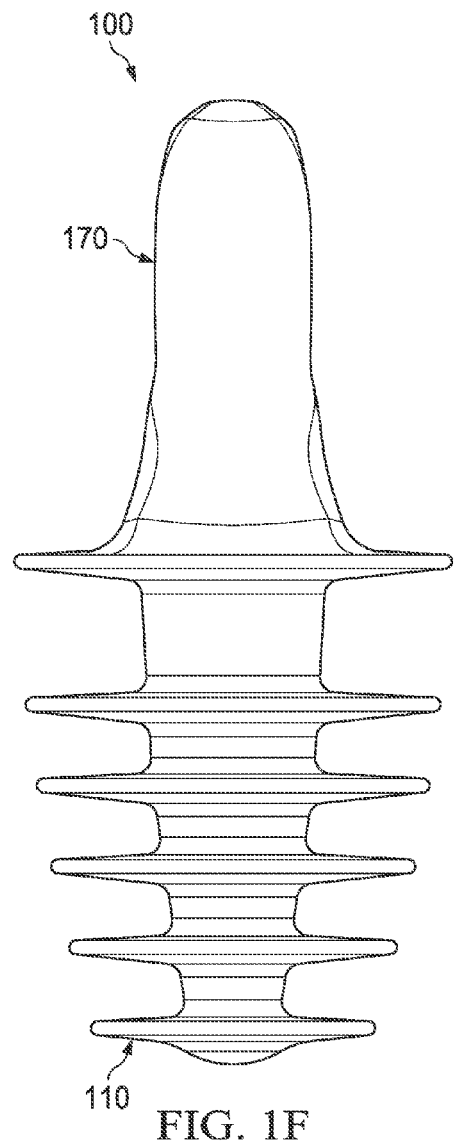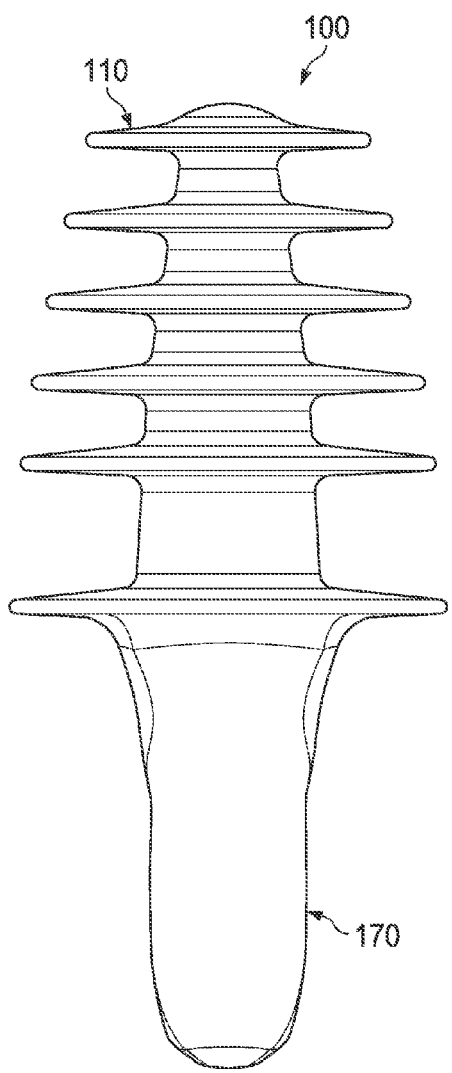
FIG. 1F
FIG. 1G

D

C

D

C

D

C

D

C

D

C

D

C

D

C

D

C

EARPIECES, SYSTEMS, AND METHODS

CROSS-REFERENCE TO RELATED APPLICATIONS

This application is a continuation-in-part of U.S. Design application No. 29/446,576 filed Feb. 25, 2013. The contents of the above application is hereby incorporated in its entirety by reference.

FIELD OF THE DISCLOSURE

The present disclosure relates, in some embodiments, to devices, systems, and methods for modifying received and/or perceived sound.

BACKGROUND OF THE DISCLOSURE

Under various circumstances, a person may wish to alter received and/or perceived sound. For example, a person may wish to reduce the volume of ambient sound. Over ear solutions, however, may suffer disadvantages such as, for example, requiring a user to tolerate otherwise unwanted bulk. In ear solutions may be uncomfortable, poorly fitted and/or fail to provide desired reduction in sound.

SUMMARY

Accordingly, a need has arisen for improved devices, systems, and methods for modifying received and/or perceived sound. The present disclosure relates, according to some embodiments, to devices, systems, and methods for modifying received and/or perceived sound. For example, a device for altering sound received at a subject's ear may comprise an elongated earpiece having a proximal portion and a distal portion and defining a longitudinal axis (e.g., together defining a longitudinal axis). A proximal portion may comprise an insert configured for at least partial insertion in the canal of the subject's ear. An insert may comprise a first elongated stem positioned generally parallel to the longitudinal axis and tapering from its distal end to its proximal end, at least 3 insert flanges (e.g., 4, 5, 6), each insert flange fixed along the length of the stem generally perpendicular to the longitudinal axis, and/or a stop flange fixed to the stem distal to the insert flanges at its distal end and having an outer periphery with a major extent and a minor extent with the major extent greater than the minor extent. A distal end may comprise a handle configured to guide insertion of the insert in the subject's ear canal.

In some embodiments, each insert flange has an outer periphery that is independently selected from the group consisting of generally circular, generally oval, generally elliptical, generally lunar, and asymmetric. Each insert flange may be independently generally planar with a major axis and a minor axis and/or dimensioned to have an extent along its major axis that is about 1× to about 4× its extent along its minor axis. A stop may have an oblong outer periphery that is independently selected from the group consisting of generally oval, generally elliptical, generally lunar, and asymmetric. A stop flange may be generally planar with a major axis and a minor axis and/or dimensioned to have an extent along its major axis that is about 1× to about 4× its extent along its minor axis.

Each insert flange may be independently fixed at its center to a stem in some embodiments. Insert flanges may vary (independently) in size with the smallest having, for example, the most proximal stem position. The largest insert flange may have, for example, the most distal stem position. A stem, according to some embodiments, may curve away from the longitudinal axis at its proximal end.

An insert may further comprise a second elongated stem positioned generally parallel to the longitudinal axis and tapering from its distal end to its proximal end, wherein each insert flange is fixed along the length of the second stem generally perpendicular to the longitudinal axis according to some embodiments. A two-stem insert may further comprise an aperture along the longitudinal axis, the aperture at least partially defined by the first stem and the second stem. An insert may further comprise a third elongated stem positioned generally parallel to the longitudinal axis and tapering from its distal end to its proximal end, wherein each insert flange is fixed along the length of the third stem generally perpendicular to the longitudinal axis. A three-stem insert may further comprise an aperture along the longitudinal axis, the aperture at least partially defined by the first stem, the second stem, and the third stem.

In some embodiments, the at least 3 insert flanges are evenly spaced apart from each other and from the stop flange. Insert flanges may be spaced apart from each other along the stem by a first distance ($d_1$) and the most distal insert flange may be spaced apart from the stop flange by a second distance ($d_2$). The first distance ($d_1$) may be, for example, about 25% to about 100% of the second distance ($d_2$).

A handle may comprise a generally cylindrically shaped body, a generally ovally shaped body, a generally triangularly shaped body, a generally fish-tail shaped body, and an asymmetric body according to some embodiments. A handle may comprise a generally planar body having a first lateral surface and a second lateral surface. The first lateral surface may comprise a first lateral recess configured to contact a human finger and the second lateral surface may comprise a second lateral recess configured to contact a human thumb. A handle plane may comprise the longitudinal axis or be parallel or substantially parallel to the longitudinal axis. A handle plane may comprise at least one flange major axis or be parallel or substantially parallel to at least one flange major axis. A handle plane may comprise a major axis of a stem section or be parallel or substantially parallel to a major axis of a stem section.

A handle may further comprise at least one through hole from the first lateral surface to the second lateral surface. A handle may further comprise, in some embodiments, a generally cylindrical body extending distally from the insert and a support having a first end fixed to the distal end of the body and a second end fixed to at least a portion of a distal surface of the stop flange. A handle body, a handle support, and a stop flange may have a generally triangular periphery and define a first lateral surface comprising a first lateral recess and a second lateral surface comprising a second lateral recess. A stop flange may be thicker than the insert flanges.

The present disclosure relates, according to some embodiments, to earpiece systems. A system may comprise, for example, at least two earpieces. Earpieces in a system may be have an identical configuration or may have a handed configuration (e.g., left and right). A system may comprise a cord having two ends with each end fixed or removeably attached to an earpiece. A system may comprise in some embodiments, a speaker in acoustic communication (e.g., unimpeded communication) with a subject's ear. An earpiece system may comprise, an amplifier, a processor, a memory, a receiver, a transmitter, and combinations thereof.

BRIEF DESCRIPTION OF THE DRAWINGS

Some embodiments of the disclosure may be understood by referring, in part, to the present disclosure and the accompanying drawings, wherein:

FIG. 1F illustrates a first edge view of a device for installation in a subject's ear according to a specific example embodiment of the disclosure;

FIG. 1G illustrates a second edge view of a device for installation in a subject's ear according to a specific example embodiment of the disclosure;

Figure 1A:
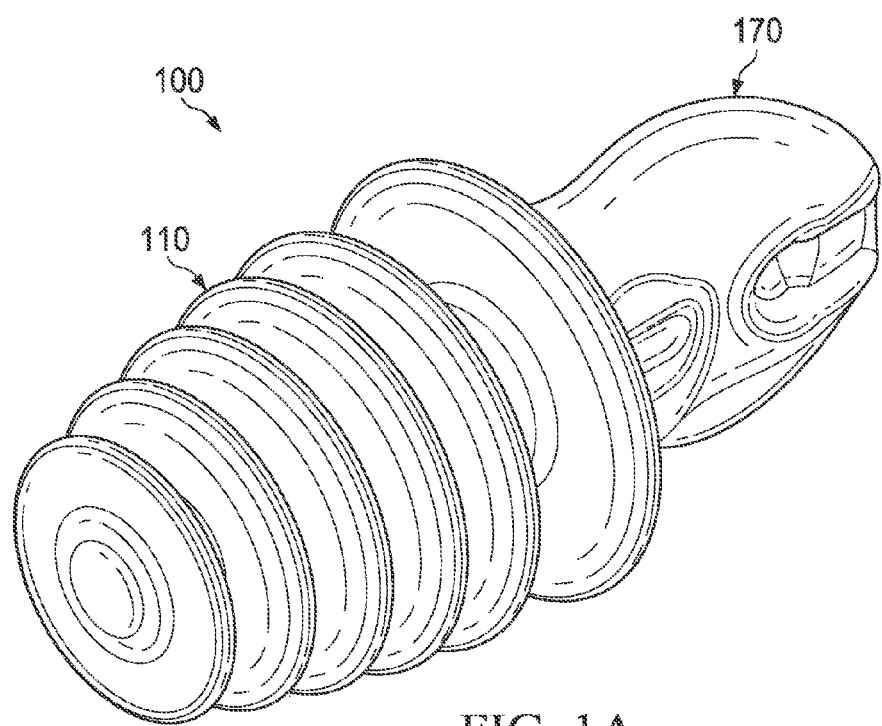
FIG. 1A illustrates a perspective view of a device for installation in a subject's ear according to a specific example embodiment of the disclosure.

Table 1 below includes the reference numerals used in this application. The thousands and hundreds digits correspond to the figure in which the item appears while the tens and ones digits correspond to the particular item indicated. Similar structures share matching tens and ones digits.

| Description | 1 | 2 | 3 | 4 | 5 | 6 | 7 | 8 | 9 | 10 | 11 |
|---|---|---|---|---|---|---|---|---|---|---|---|
| Earpiece | 100 | 200 | 300 | 400 | 500 | 600 | 700 | 800 | 900 | 1000 | 1100 |
| Longitudinal axis | 103 | 203 | 303 | 403 | 503 | 603 | 703 | | | | |
| Major flange axis | 105 | 205 | | | | | | | | | |
| Minor flange axis | 107 | 207 | | | | | | | | | |
| Insert | 110 | 210 | 310 | 410 | 510 | 610 | 710 | 810 | 910 | 1010 | 1110 |
| Flange set | 120 | 220 | 320 | | | | | | | | |
| Stop flange | 121 | 221 | 321 | 421 | 521 | 621 | 721 | 821 | 921 | 1021 | 1121 |
| Flange | 122 | 222 | 322 | 422 | 522 | 622 | 722 | 822 | 922 | 1022 | 1122 |
| Flange | 123 | 223 | 323 | 423 | 523 | 623 | 723 | 823 | 923 | 1023 | 1123 |
| Flange | 124 | 224 | 324 | 424 | 524 | 624 | 724 | 824 | 924 | 1024 | 1124 |
| Flange | 125 | 225 | 325 | 425 | 525 | 625 | 725 | 825 | 925 | 1025 | 1125 |
| Flange | 126 | 226 | | | | | | | | | |
| Flange gap | 129 | | | | | | | | 929 | 1029 | 1129 |
| Stem | 130 | 230 | | | | 630 | 730 | 830 | 930 | 1030 | 1130 |
| Stem member | 131 | 231 | 331 | 431 | 531 | 631 | 731 | 831 | 931 | 1031 | |
| Stem member | 132 | 232 | 332 | 432 | 532 | 632 | 732 | | 932 | 1032 | |
| Stem member | 133 | 233 | 333 | 433 | 533 | 633 | 733 | 833 | 933 | 1033 | |
| Stem member | 134 | 234 | 334 | 434 | 534 | 634 | 734 | 834 | 934 | 1034 | |
| Stem member | 135 | 235 | | 435 | | | | | | | |
| Aperture | | | | 436 | | 636 | | | | | |
| Aperture | | | | 437 | | 637 | | | | | |
| Aperture | | | | 438 | | 638 | | | | | |
| Aperture | | | | 439 | | 639 | | | | | |
| Superior stem | | | | | | 640 | | | | | |
| Stem member | | | | | | 641 | | | | | |
| Stem member | | | | | | 642 | | | | | |
| Stem member | | | | | | 643 | | | | | |
| Stem member | | | | | | 644 | | | | | |
| Inferior stem | | | | | | 650 | | | | | |
| Stem member | | | | | | 651 | | | | | |
| Stem member | | | | | | 652 | | | | | |
| Stem member | | | | | | 653 | | | | | |
| Stem member | | | | | | 654 | | | | | |
| Handle | 170 | 270 | 370 | 470 | 570 | 670 | 770 | 870 | 970 | 1070 | 1170 |
| Neck | 171 | 271 | | 471 | 571 | | | | | | 1171 |
| Recess | 172 | 272 | | 472 | 572 | | 772 | | 972 | 1072 | 1172 |
| Body | 173 | 273 | | 473 | 573 | | | 873 | | | 1173 |
| Recess | 174 | 274 | 374 | | | | | | | | |
| Aperture | 175 | 275 | | | | | 775 | 875 | 975 | | |
| Shoulder | | 276 | | | | | | | | | |
| Lateral shoulder | | | | | 577 | | | | | | 1177 |
| Support | | | | | | | 778 | 878 | 978 | 1078 | |
| Protrusion | | | | | | | | 879 | | | |
| Stem | | | | | | 680 | | | | | |
| Body | | | | | | 681 | | | | | |
| Protrusion | | | | | | 682 | | | | | |
| Aperture | | | | | | 683 | | | | | |
| Frame | | | | | | 690 | | | | | |
| Frame member | | | | | | 691 | | | | | |
| Neck | | | | | | 692 | | | | | |
| Tail | | | | | | 693 | | | | | |

DETAILED DESCRIPTION

The present disclosure relates, according to some embodiments, to devices, systems, and methods for modifying received and/or perceived sound. Devices, systems, and methods may alter received and/or perceived sound by reducing, muffling, dampening, attenuating, and/or otherwise lowering (collectively "reducing") the ambient sound that enters the ear canal and/or reaches the eardrum in some embodiments. All or substantially all ambient sound may be reduced and/or selected sounds and/or frequencies may be reduced. According to some embodiments, devices, systems, and methods may be compatible with and optionally include producing a desired sound at or in a subject's ear (e.g., music active noise canceling, or two-way communication). A device, in some embodiments, may comprise an earpiece capable of being worn at or in a subject's ear. For example, earpieces may include earplugs (hearing protection or other sound attenuation), earphones (music, communication, and the like), and/or hearing aid tips (amplification of external sound).

Devices—Earpieces

According to some embodiments, an earpiece may have a proximal end and a distal end. A proximal end may comprise an inserted portion configured to be installed in a subject's ear. A distal end may facilitate placing, adjusting, and/or removing the proximal end. An earpiece may comprise a handle and an insert according to some embodiments. An earpiece may define a plane (e.g., a symmetry plane) and/or axis (e.g., a longitudinal axis) along is length.

A handle may comprise a body configured to be grasped and/or facilitate installation in a subject's ear in some embodiments. A handle may have any desired shape to support and/or facilitate installation of an earpiece at a subject's ear. For example, a handle may have a generally cylindrical form aligned with an earpiece longitudinal axis. An outer periphery of a section plane of a handle taken perpendicular or substantially perpendicular to an earpiece longitudinal axis may define an elongated or oblong shape in some embodiments. A major axis of an elongated section may be generally vertical and a minor axis may be generally horizontal, relative to a subject in an upright position. In some embodiments, a handle may include one or more recesses, apertures, supports, ridges, and/or other contours for an ergonomic grip. A handle may be configured (e.g., arranged, dimensioned) to prevent, substantially prevent, and/or reduce bending in unwanted directions and/or to assist by bending in guiding earpiece into ear canal. In some embodiments, a handle may be configured to receive a cord (e.g., connecting two earpieces). A handle may be configured, for example, to receive a cord in manner that does not interfere with, enhances, and/or completes an ergonomic grip. For example, a divot may be included in a handle to allow for ergonomic grip when a cord is in place.

A handle may serve one or more purposes, according to some embodiments. For example, a handle may (a) support and/or enhance a subject's ability to insert an earpiece in an ear canal, (b) provide rigidity of soft/comfortable earpiece to prevent improper insertion, (c) increase the likelihood of correct insertion (e.g., to provide user with maximum sound attenuation), (d) provide a tactilely comfortable for inserting and/or adjusting earpiece position.

An insert may comprise an elongate member having a longitudinal axis and configured for insertion in a subject's ear. For example, an insert may have a generally cylindrical shape with a generally circular peripheral extent (e.g., perpendicular to a longitudinal axis). A peripheral extent of an insert may have any desired symmetric or asymmetric shape according to some embodiments. For example, a peripheral extent of an insert may be any curvilinear shape including circular, oval, ellipsoid, lune, and the like. A peripheral extent of an insert, according to some embodiments, may be asymmetric along one, two, and/or three cardinal axes. For example, a section of a peripheral extent of an insert taken perpendicular to a longitudinal axis may have 0, 1, or 2 axes of symmetry.

In some embodiments, elongate member of an insert may comprise an elongated stem defining a longitudinal axis and one or more flanges spaced apart along and oriented generally perpendicular to the longitudinal axis. Flanges may be configured to contact one or more points in a subject's ear canal. Flanges may define a peripheral extent of an insert and have any curvilinear shape. A flange may have a vertical axis (e.g., major axis) generally perpendicular to a longitudinal insert axis and generally parallel to a vertically positioned subject (e.g., subject's head). A flange may have a lateral or horizontal axis (e.g., minor axis) generally perpendicular to a longitudinal insert axis and generally perpendicular to a vertical axis. Flanges may have any desired shape including, according to some embodiments, a shape that is and/or is intended to substantially match the shape of a subject's ear canal. For example, a flange may be dimensioned to have an extent along its major axis that is about 1× to about 4× its extent along its minor axis (e.g., >~1×, >~1.25×, >~1.5×, 1.75×, >~2×, >~2.5×, <~3×, <~3.5×, <~4×, and combinations thereof). The longitudinal, major, and/or minor extent of a flange may be selected as desired (e.g., to seal and fit a non-circular ear canal). For example, the dimensions of a flange may be adjusted to maximize the amount of material occluding and/or blocking sound while minimizing excess material that causes discomfort.

According to some embodiments, an earpiece may comprise a plurality of flanges. Flanges may be numbered according to their position, for example, along a longitudinal earpiece axis (e.g., proximal to distal, distal to proximal). A flange positioned at a distal end of an insert may be shaped and dimensioned differently than other flanges in some embodiments. For example, a distal flange (e.g., a first flange, when numbered distal to proximal) may comprise a larger and/or thicker flange configured to provide a stop (e.g., absolute stop) point for earpiece insertion, an orientation indicator, feedback (e.g., contact with external ear structures) to signal complete insertion, and/or combinations thereof.

An earpiece having at least two flanges may be configured, in some embodiments, to have a gap between successive flanges along a longitudinal axis. Gaps may be numbered as desired, for example, like flanges. Flanges numbered from distal to proximal may have a first gap between first and second flanges, a second gap between second and third flanges, and a third gap between third and fourth flanges, for example. A gap (e.g., a distal gap) may facilitate insertion by acting as a fulcrum point when pressing an earpiece into an ear canal. A larger gap (e.g., a larger distal gap) may allow an earpiece to be seated deeper into an ear canal, positioning the flanges (e.g., more proximal flanges) in a more desirable (e.g., optimum) location. For example, a larger gap may allow an earpiece to be seated deeper in an ear canal, form a better seal in the ear canal, and/or create a better fitting earpiece. In some embodiments, an earpiece may comprise four insert flanges arranged along a stem and a distally positioned stop flange. Insert flanges may be spaced apart from each other along the stem by a first distance ($d_1$) and the most distal insert flange is spaced apart from the stop flange by a second distance ($d_2$). According to some embodiments, the first distance may be less than or equal to the second distance. For example, the first distance ($d_1$) may be more than about 25% of the second distance ($d_2$), the first distance ($d_1$) may be more than about 30% of the second distance ($d_2$), the first distance ($d_1$) may be more than about 35% of the second distance ($d_2$), the first distance ($d_1$) may be more than about 40% of the second distance ($d_2$), the first distance ($d_1$) may be more than about 45% of the second distance ($d_2$), the first distance ($d_1$) may be more than about 50% of the second distance ($d_2$), the first distance ($d_1$) may be more than about 55% of the second distance ($d_2$), the first distance ($d_1$) may be more than about 60% of the second distance ($d_2$), the first distance ($d_1$) may be more than about 65% of the second distance ($d_2$), the first distance ($d_1$) may be more than about 70% of the second distance ($d_2$), the first distance ($d_1$) may be more than about 75% of the second distance ($d_2$), the first distance ($d_1$) may be more than about 80% of the second distance ($d_2$), the first distance ($d_1$) may be more than about 85% of the second distance ($d_2$), the first distance ($d_1$) may be more than about 90% of the second distance ($d_2$), and/or the first distance ($d_1$) may be more than about 95% of the second distance ($d_2$), In some embodiments, the first distance ($d_1$) may be about 25% to about 100% of the second distance ($d_2$). The actual distances between flanges may vary independently of one another and/or may be a function of other dimensions of an earpiece and/or the size of a subject or subjects ear canal according to some embodiment. For some specific example embodiments, the distance between the two most distal flanges (e.g., a distal-most insert flange and a stop flange) may be about 2 mm to about 8 mm. Any two up to all flanges in an earpiece may be similarly shaped and/or dimensioned, according to some embodiments. For example, similarly shaped flanges may have different sizes, generally arranged in size order with the smallest flange in the most proximal position (e.g., deepest within the ear) and the largest flange (e.g., a stop flange) located in the most distal position.

In some embodiments, an insert may comprise a stem. Up to all flanges in an earpiece may be mounted on a stem. For example, a stem may extend to, through, and/or between included flanges. A stem may be positioned along, substantially along, parallel, or substantially parallel to a longitudinal axis of an insert. A stem may have any desired shape and/or dimensions. For example, a stem may have an elongated form generally parallel to a longitudinal axis with a peripheral extent that is smaller (e.g., substantially smaller) than the peripheral extent of a flange. For example, a stem may have a maximum dimension in a plane perpendicular to the longitudinal axis that is about 25% to about 95% of the lateral extent of the smallest attached flange. A section of a stem along a plane generally perpendicular to a longitudinal axis may define a non-circular outer periphery, in some embodiments. A non-circular stem may extend from the handle to the deepest flange that penetrates the ear canal with attached flanges. A non-circular stem may have an oblong profile with the major axis oriented vertically or substantially vertically and a minor axis oriented laterally or substantially laterally. A non-circular inner central post may extend from the handle to the deepest flange that penetrates the ear canal with attached flanges in some embodiments. A non-circular stem may support (e.g., encourage) a stem to bend more in a lateral direction (e.g., anterior-posterior) and/or reduce vertical bending. According to some embodiments, a non-circular stem may provide flexibility to follow the natural curvature of the ear canal during insertion (e.g., making insertion easier) and/or may provide long term comfort. A stem (e.g., a non-circular stem) may have its major and/or minor axes generally aligned respectively with major and/or minor axes of a handle (e.g., non-circular handle), and/or a first (e.g., most distal) flange. A directionally guiding handle may include a handle co-aligned with a stem and/or flanges in some embodiments. Co-alignment may permit a specially shaped handle to properly or optimally index or align or locate flanges in specific orientations in the ear canal for maximum occlusion. In some embodiments, a handle may be configured to allow more intuitive orientation of the earpiece based on natural ergonomics of the handle relative to the human hand and/or non-circular flanges to be oriented in accord with the shape of an ear canal.

A stem, in some embodiments, may be connected independently to any desired point on each successive flange. A stem may be connected at or near the center of each flange. According to some embodiments, a stem may connect to each flange at a desired (e.g., constant) distance from a selected edge. For example, a stem may be positioned about 1 mm to about 10 mm from an upper edge of all flanges in an earpiece. A stem may have a superior bias (e.g., toward the upper edge) or an inferior bias (e.g., toward the lower edge). A stem may contact a flange superiorly (nearer the flange's upper edge) or inferiorly (nearer the flange's lower edge).

A stem may have a constant lateral and/or vertical extent all along a longitudinal axis, in some embodiments. A stem may taper in its lateral and/or vertical extent at points closer to a proximal and/or distal end. The amount of taper may change over the length of the stem in some embodiments. For example, a stem may taper by 2% per 10% length of the handle at the distal end and 15% per 10% length of the handle at the proximal end. Such a taper may vary along different axes—horizontally it may taper less than vertically, for example, to accommodate more variation in the natural human ear further in. Human ear canals may be more varied in the horizontal direction at greater depths into the canal.

In some embodiments, a stem may be curved. For example, a stem may be curved in a generally vertical plane, relative to a subject in an upright position. A stem curvature may progress from a distal, generally superior position to a proximal, generally inferior position along a length of the stem, in some embodiments. A stem curvature may be disposed, according to some embodiments, from handle to innermost flange and/or curved towards top or back of a subject's head relative to direction of straight insertion. Stem curvature may be configured to allow easier insertion of the earpiece by mimicking the natural curvature of the ear canal (ear canals are not straight). In some embodiments, long-term comfort may be enhanced with a stem curved to mimic a natural curvature of an ear canal. For example, a curved stem may not exert a force (or as much force) on the ear canal wall as a straight stem would. A stem curvature may be extended into and/or aligned with a handle curvature.

In some embodiments, an earpiece may comprise a directionally guiding handle and a curved stem, wherein the handle and stem are generally aligned. For example, a handle may comprise a surface to contact a subject's figure and a surface to contact a subject's thumb, wherein the surfaces are on opposite sides of a handle plane. A handle (e.g., a handle plane) may be fixed to an insert at any desired degree of rotation. According to some embodiments, a longitudinal axis (e.g., of a stem or an earpiece) may lie within a handle plane or extend parallel to a handle plane. A stem may be curved, in some embodiments such that it defines a plane of curvature. According to some embodiments, a plane of stem curvature may be parallel or substantially parallel to a handle (e.g., a handle plane). A handle (e.g., a handle plane) may be positioned perpendicular or substantially perpendicular to one or more flanges (e.g., flange planes). In some embodiments, an earpiece so configured may aid a user in properly positioning an insert (e.g., a curved stem, flanges) for maximum occlusion and/or ease of insertion.

An earpiece (e.g., an insert) may comprise, in some embodiments, two or more stems connecting flanges to one another and to the handle. For example, an earpiece (e.g., an insert) comprising two stems may have an aperture positioned generally between the stems. An earpiece (e.g., an insert) comprising three stems may be configured with the stems generally aligned with and spaced around a longitudinal axis, for example, forming section plane in which the three stems form the points of a triangle with an aperture positioned in the middle. In some embodiments, an earpiece (e.g., an insert) comprising three stems may be configured with the stems generally coplanar with each other. The center stem may be generally parallel with a longitudinal axis and/or may be flanked by apertures (e.g., between stems). Apertures may be partially defined (e.g., on two generally parallel sides) by stems and/or partially defined (e.g., on two generally parallel sides) by flanges. Multiple stem members may interconnect two or more flanges, in some embodiments, which may result in flexing (e.g., more uniform flexing) of the flanges during insertion, adjusting, and/or removal. Earpieces having multiple stems may place more material in an ear canal, which may increase sound attenuation while controlling a force exerted on an ear canal. Earpieces with a plurality of stems may enhance comfort by altering bending forces to decrease pressure on an ear canal.

According to some embodiments, an earpiece may comprise multiple stems in both an insert and a handle. For example, an earpiece may comprise two stems positioned generally along the earpiece's length and extending through the insert and the handle. Interconnecting multiple stems between handle and stem may allow a subject to manipulate the handle (e.g., distal portions of the stems) to cause connected flanges to collapse in some embodiments. For example, squeezing a handle may result in a corresponding movement of proximal ends of the stems along with attached flanges. A subject using an earpiece with multiple stems may have an easier, more comfortable insertion experience.

Compositions

The present disclosure relates, in some embodiments, to materials suitable for use in an earpiece. For example, an earpiece may comprise a material with a Shore A (hardness) of about 0 to about 80. Earpiece materials may have a shear modulus of about 0.1 MPa to about 20 MPa in some embodiments. An earpiece may comprise materials having a ratio of body temperature shear modulus to room temperature shear modulus greater than 0 and less than 1.0. In some embodiments, an earpiece may comprise a material with a glass transition temperature below about body temperature. An earpiece may comprise, according to some embodiments, a shape memory polymer (e.g., at any composition fraction). For example, an earpiece may comprise one or more polymers as disclosed in U.S. Pat. No. 8,299,191 and/or U.S. Patent Application No. 61/594,508.

Systems

The present disclosure relates, according to some embodiments, systems for modifying received and/or perceived sound. A system may comprise, for example, a pair of earpieces configured for use in a subject's left and right ear. In some embodiments, a system may comprise a cord fixed at a first end to a first earpiece and fixed at its second end to a second earpiece. A system may comprise, in some embodiments, a container sized to enclose one or more earpieces and/or cords.

In some embodiments, a system may include one or more inserts configured to produce sound. For example, an earpiece may comprise a stem having a cavity and/or a hollow portion in acoustic communication with a speaker. Sound may travel from the speaker through the hollow portion to a subject's ear. According to some embodiments, a stem that is at least partially hollow (e.g., having a cavity and/or a hollow portion) may be fitted with a speaker for delivering sound to a subject's ear. A system comprising an insert may be useful for delivering to a subject's ear music, amplified sound, and/or selected ambient sound. A system may further comprise components for two-way communication (e.g., a microphone, a transmitter, and/or a receiver).

Methods of Making

The present disclosure relates, in some embodiments, to methods for making an earpiece. For example, a method may include forming the earpiece into the desired form using processing equipment like blow molding, injection molding, resin transfer molding, rotational molding, foaming, casting, and the like. Another example is to use a subtractive process like machining. An earpiece may be formed (e.g., molded) as a single piece through either a single step process as described in the previous two sentences or multistep processes like overmolding.

Methods of Use

The present disclosure relates to methods for altering the sound received and/or perceived at a subject's ear (e.g., tympanic membrane). For example, a method for reducing sound received at a subject's ear (e.g., tympanic membrane) may comprise installing an earpiece in the subject's ear, wherein the earpiece has a structure according to any of the embodiments discloses herein. In some embodiments, the sound reduction may be assessed by any desired test or metric. For example, an earpiece may have an NRR of about 15 or more, about 17 or more, about 19 or more, about 21 or more, about 23 or more, about 25 or more, about 27 or more, and/or about 29 or more. An earpiece may have an NRR of about 15 or less (e.g., about 13 or less, about 11 or less, about 9 or less) in some embodiments.

SPECIFIC EXAMPLE EMBODIMENTS

Figure 1B:
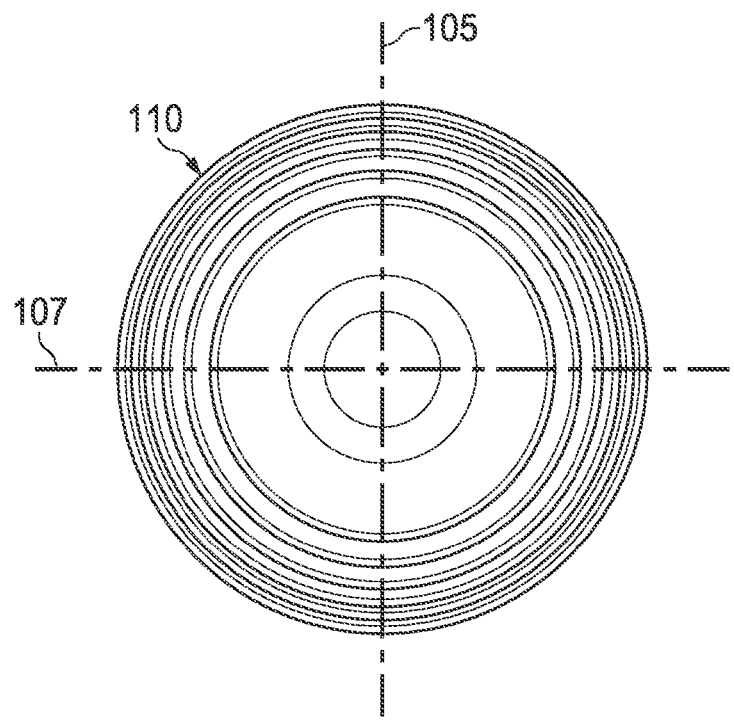
FIG. 1B illustrates a first end view of a device for installation in a subject's ear according to a specific example embodiment of the disclosure.
Figure 1C:
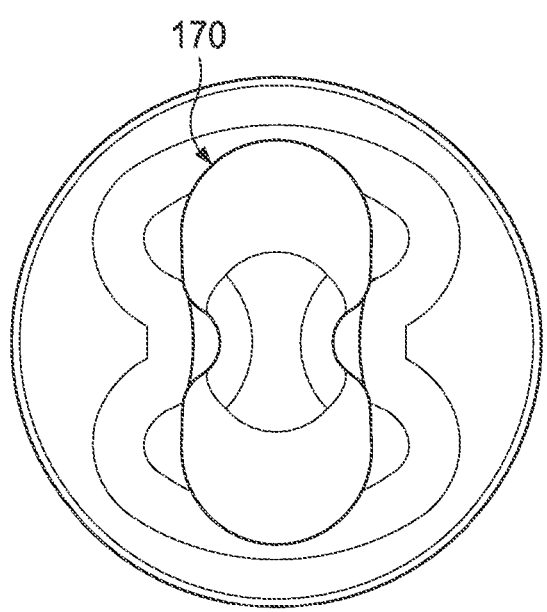
FIG. 1C illustrates a second end view of a device for installation in a subject's ear according to a specific example embodiment of the disclosure.
Figure 1D:
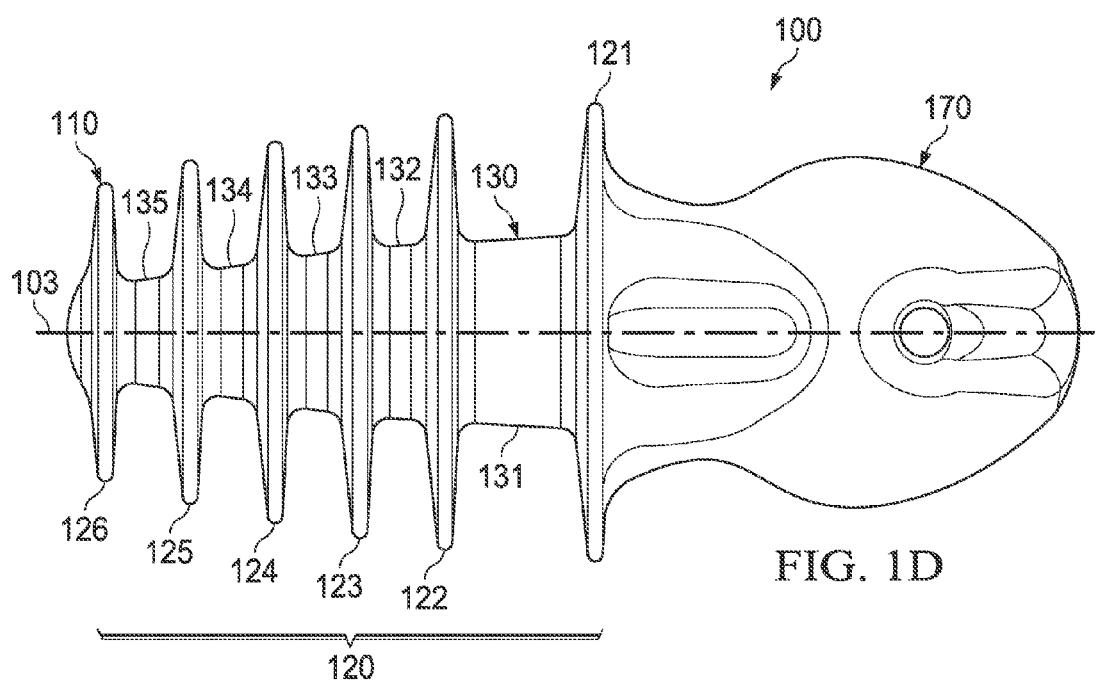
FIG. 1D illustrates a first profile view of a device for installation in a subject's ear according to a specific example embodiment of the disclosure.
Figure 1E:
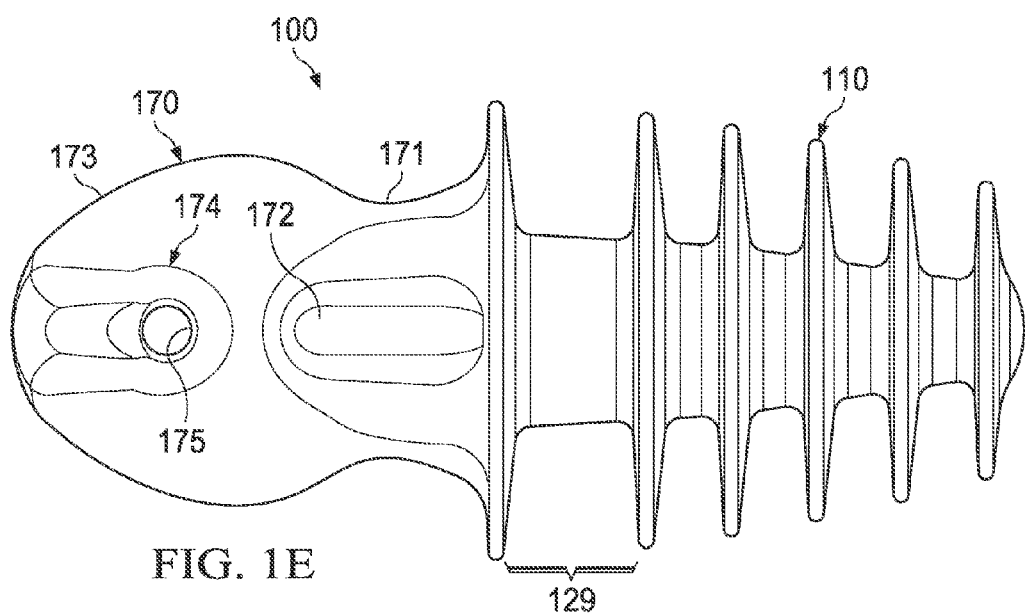
FIG. 1E illustrates a second profile view of a device for installation in a subject's ear according to a specific example embodiment of the disclosure.
Figure 1H:
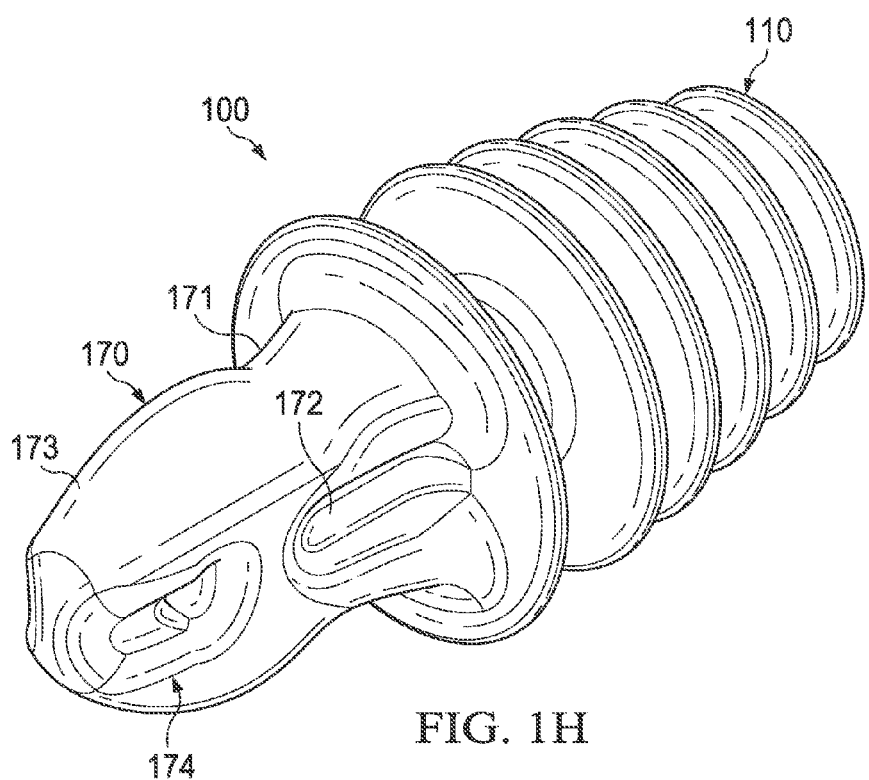
FIG. 1H illustrates a perspective view of a device for installation in a subject's ear according to a specific example embodiment of the disclosure.

Specific example embodiments of an earpiece are illustrated in FIGS. 1A-1H. Earpiece 100 comprises insert 110 and handle 170 fixed to insert 110. Insert 110 defines longitudinal axis 103 and comprises set of flanges 120 connected along stem 130. Flange set 120 comprises flange 121, flange 122, flange 123, flange 124, flange 125, and flange 126, wherein flange 121 is the largest and most distal and flange 126 is the smallest and most proximal. Flanges 121, 122, 123, 124, 125, and 126 have an extent along vertical axis 105 and along a lateral axis 107 (FIG. 1B).

Stem 130 includes stem segments 131, 132, 133, 134, and 135. These segments are defined, at least in part, by flanges 121, 122, 123, 124, 125, and 126 respectively. Stem 130 passes through the centers of generally circular flanges 121, 122, 123, 124, 125, and 126 and tapers from distal (larger) to proximal (smaller) end. Flanges 121, 122, 123, 124, 125, and 126 lie in planes generally perpendicular to axis 103. Stem segment 131 may be about twice the length of segment 132 forming flange gap 129. As shown, segments 132, 133, 134, and 134 may have substantially uniform length.

Handle 170 includes generally oval-shaped body 173 connected via neck 171 to insert 110 and centered along axis 103. Handle 170 also includes recess 172 in a thickened region at the junction between handle 170 and insert 110. Recess 172 may be contoured to complement a subject's finger tips (e.g., thumb and forefinger). At its distal end handle 170 includes recess 174 and through hole 175, which is sufficiently dimensioned to receive a cord to connect earpiece 100 with a like earpiece.

Figure 2A:
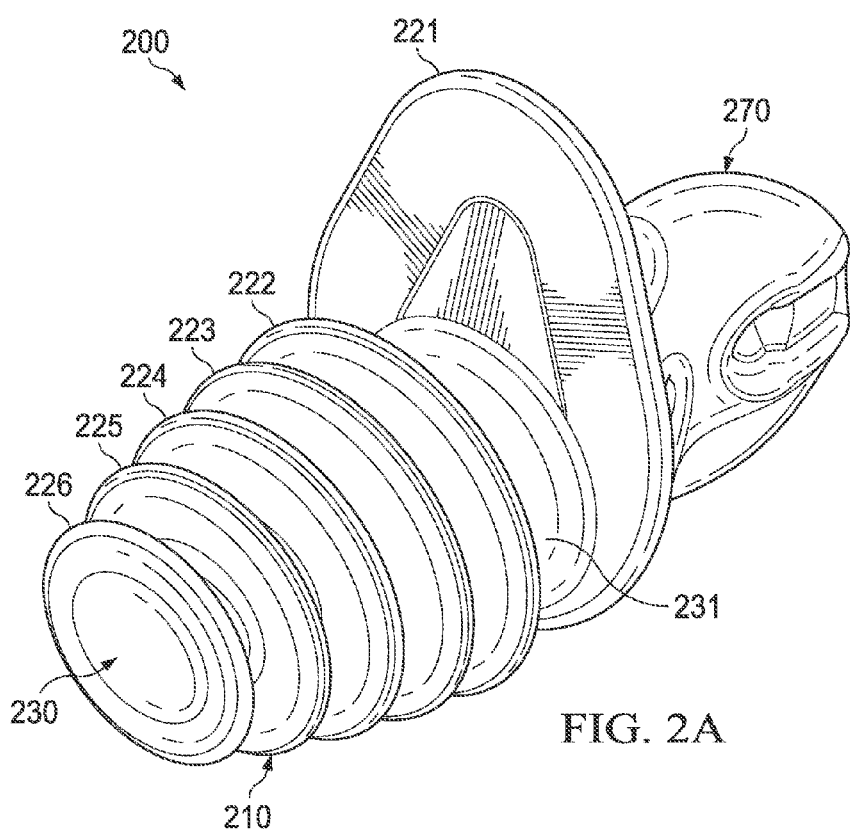
FIG. 2A illustrates a perspective view of a device for installation in a subject's ear according to a specific example embodiment of the disclosure.
Figure 2B:
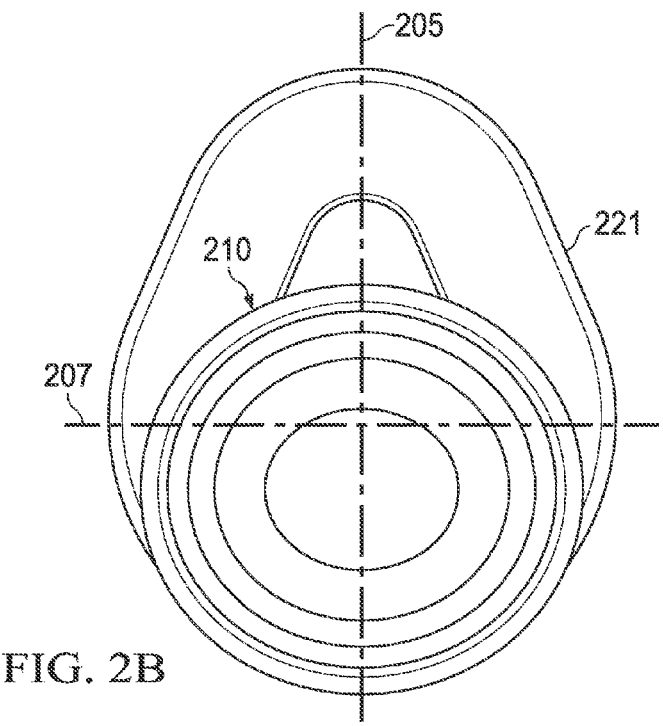
FIG. 2B illustrates a first end view of a device for installation in a subject's ear according to a specific example embodiment of the disclosure.
Figure 2C:
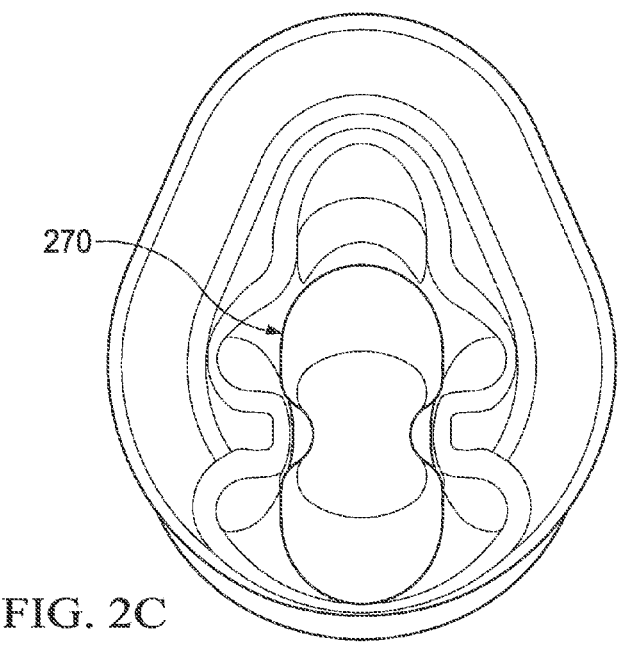
FIG. 2C illustrates a second end view of a device for installation in a subject's ear according to a specific example embodiment of the disclosure.
Figure 2D:
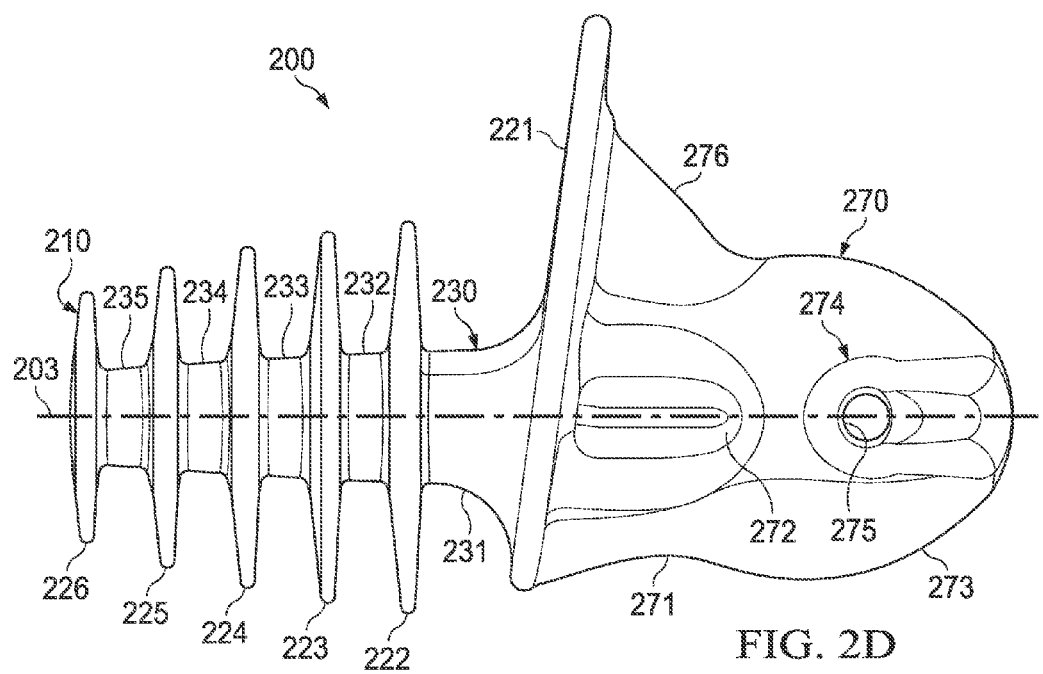
FIG. 2D illustrates a first profile view of a device for installation in a subject's ear according to a specific example embodiment of the disclosure.
Figure 2E:
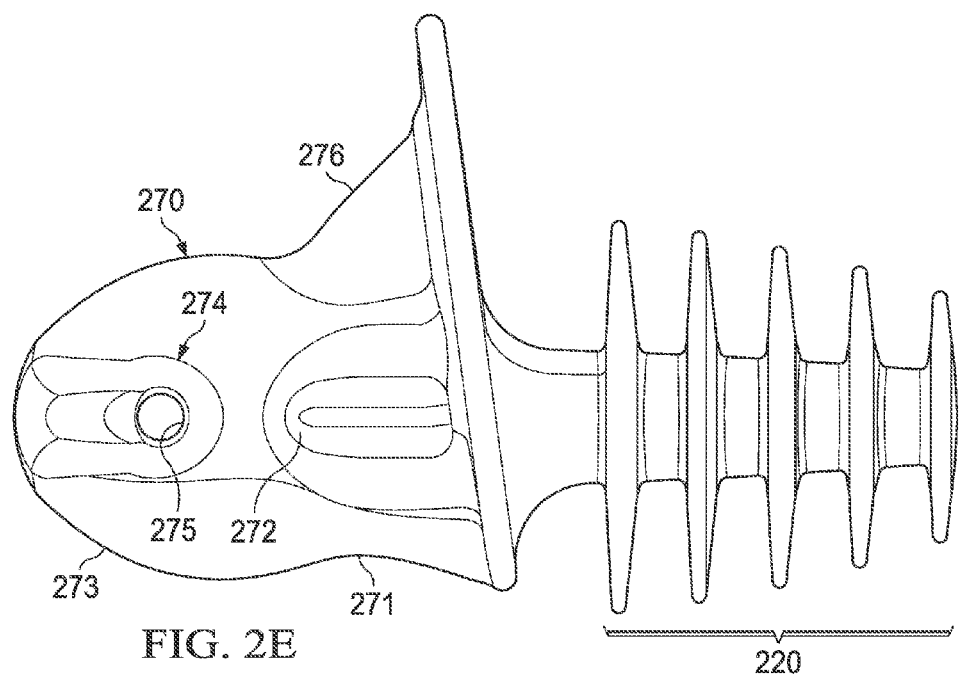
FIG. 2E illustrates a second profile view of a device for installation in a subject's ear according to a specific example embodiment of the disclosure.
Figure 2F:
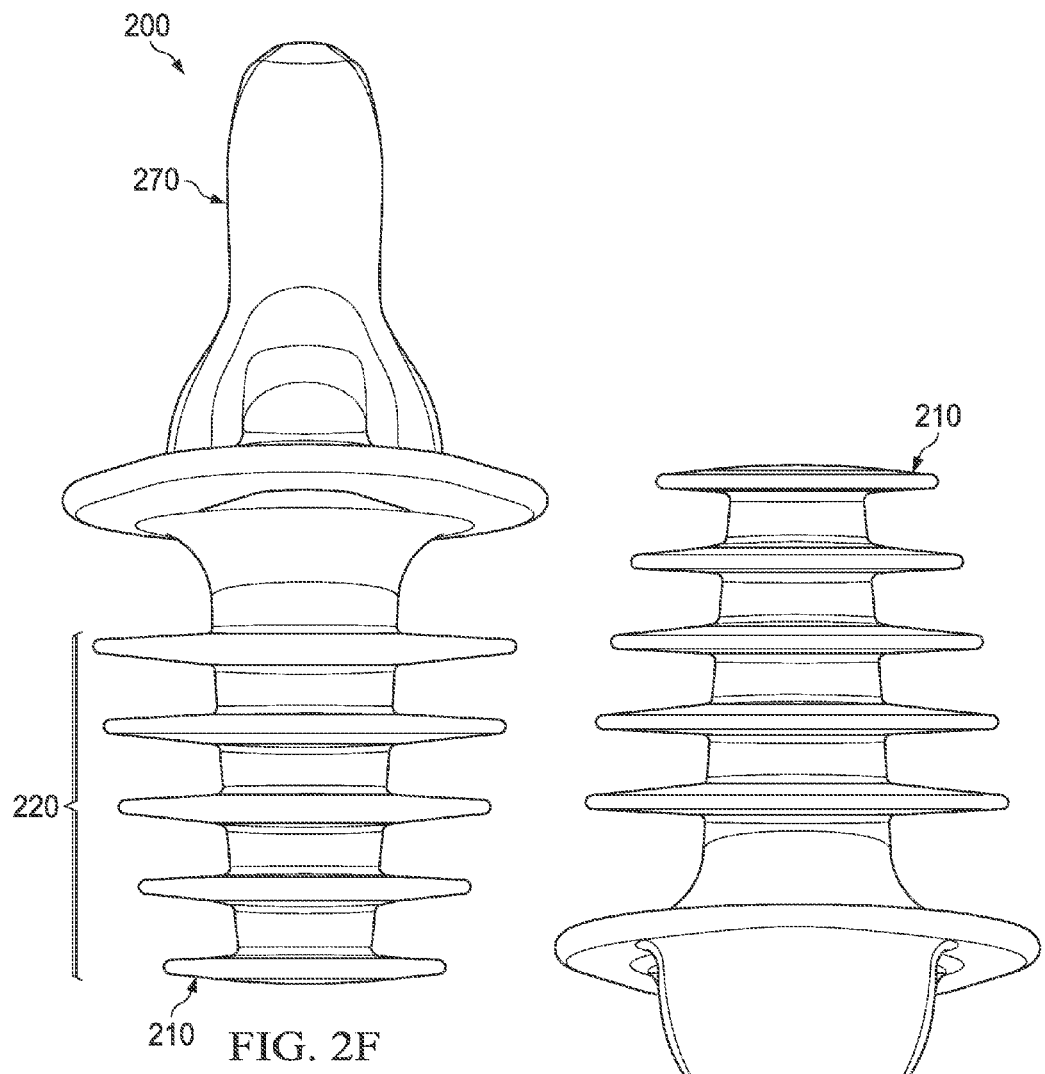
FIG. 2F illustrates a first edge view of a device for installation in a subject's ear according to a specific example embodiment of the disclosure.
Figure 2G:
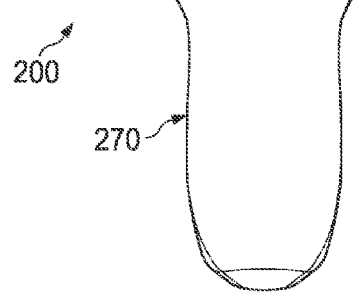
FIG. 2G illustrates a second edge view of a device for installation in a subject's ear according to a specific example embodiment of the disclosure.
Figure 2H:
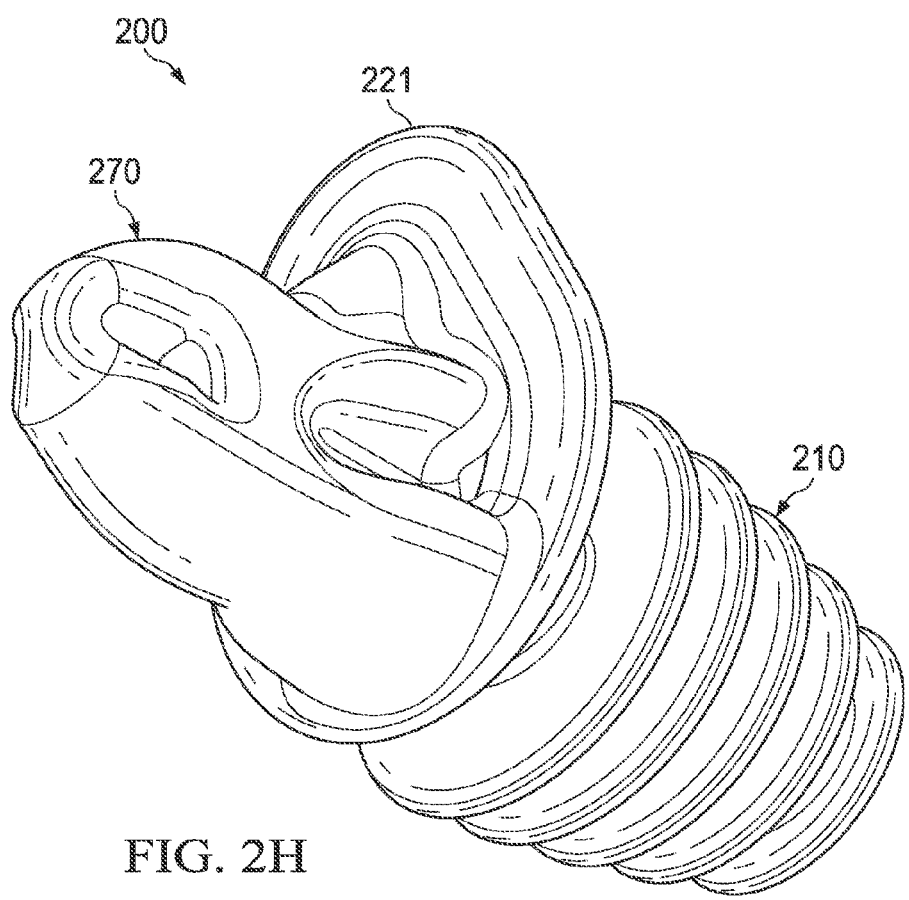
FIG. 2H illustrates a perspective view of a device for installation in a subject's ear according to a specific example embodiment of the disclosure.

Specific example embodiments of an earpiece are illustrated in FIGS. 2A-2H. Earpiece 200 comprises insert 210 and handle 270 fixed to insert 210. Insert 210 defines longitudinal axis 203 and comprises set of flanges 220 connected along stem 230. Flange set 220 comprises flange 221, flange 222, flange 223, flange 224, flange 225, and flange 226, wherein flange 221 is the largest and most distal and flange 226 is the smallest and most proximal. Flange 221 has a teardrop shape with its larger end generally centered on axis 203 and stem 230. Flanges 221, 222, 223, 224, 225, and 226 have a major extent along vertical axis 205 and a minor extent along a lateral axis 207 (FIG. 2B).

Stem 230 includes stem segments 231, 232, 233, 234, and 235. These segments are defined, at least in part, by flanges 221, 222, 223, 224, 225, and 226 respectively. Stem 230 passes through the centers of generally circular flanges 222, 223, 224, 225, and 226 and tapers from distal (larger) to proximal (smaller) end. Stem segment 231 may be about twice the length of segment 232 forming flange gap 229. As shown, segments 232, 233, 234, and 234 may have substantially uniform length. Flanges 222, 223, 224, 225, and 226 lie in planes generally perpendicular to axis 203 and flange 221 lies at an incline.

Handle 270 includes generally oval-shaped body 273 connected via neck 271 to insert 210 and positioned along axis 203. Handle 270 also includes recess 272 in a thickened region at the junction between handle 270 and insert 210. Handle 270 further includes shoulder 276 connecting flange 221 and body 273. Recess 272 may be contoured to complement a subject's finger tips (e.g., thumb and forefinger). At its distal end handle 270 includes recess 274 and through hole 275, which is sufficiently dimensioned to receive a cord to connect earpiece 200 with a like earpiece.

Figure 3A:
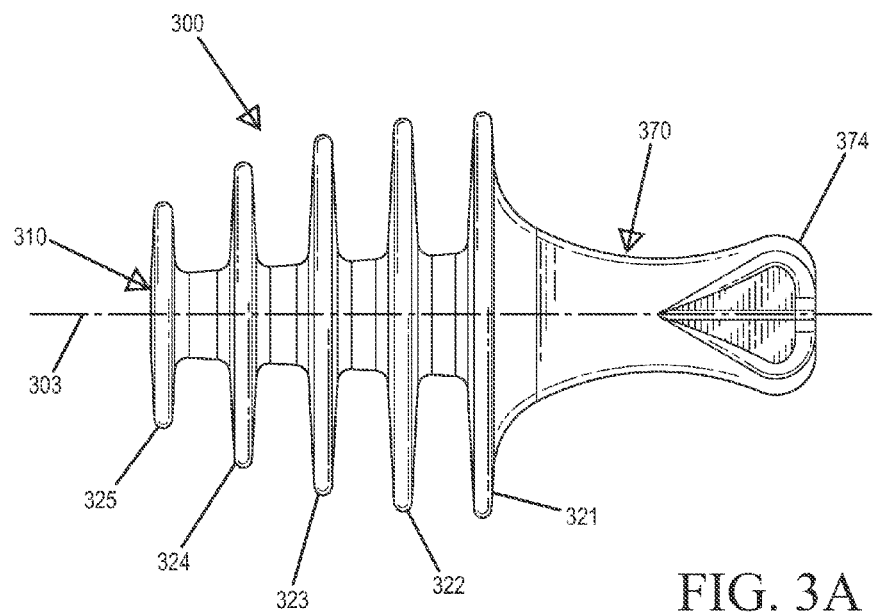
FIG. 3A illustrates a side view of a device for installation in a subject's ear according to a specific example embodiment of the disclosure.
Figure 3B:
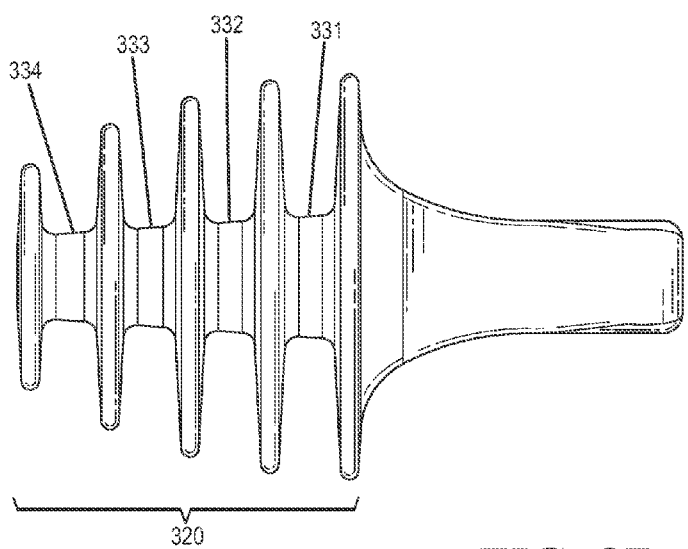
FIG. 3B illustrates a bottom view of a device for installation in a subject's ear according to a specific example embodiment of the disclosure.
Figure 3:
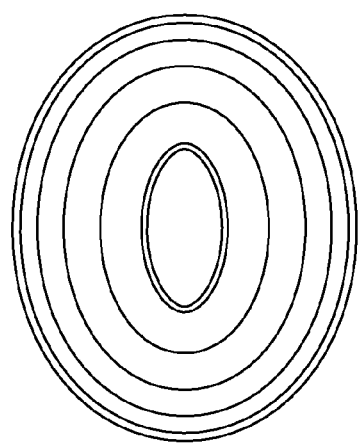
FIG. 3C illustrates a perspective view of a device for installation in a subject's ear according to a specific example embodiment of the disclosure.
FIG. 3D illustrates an end view of a device for installation in a subject's ear according to a specific example embodiment of the disclosure.
Figure 3:
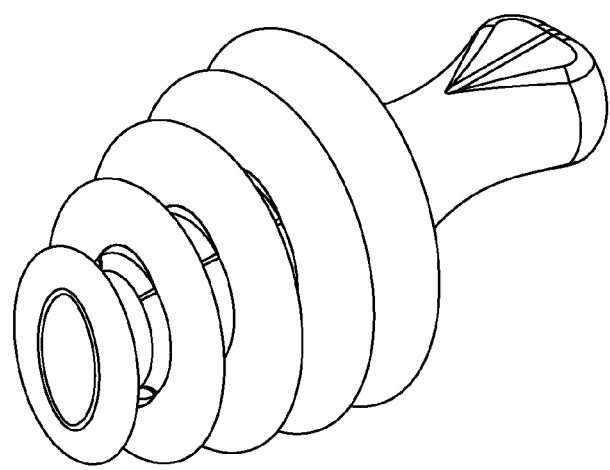
Figure 4A:
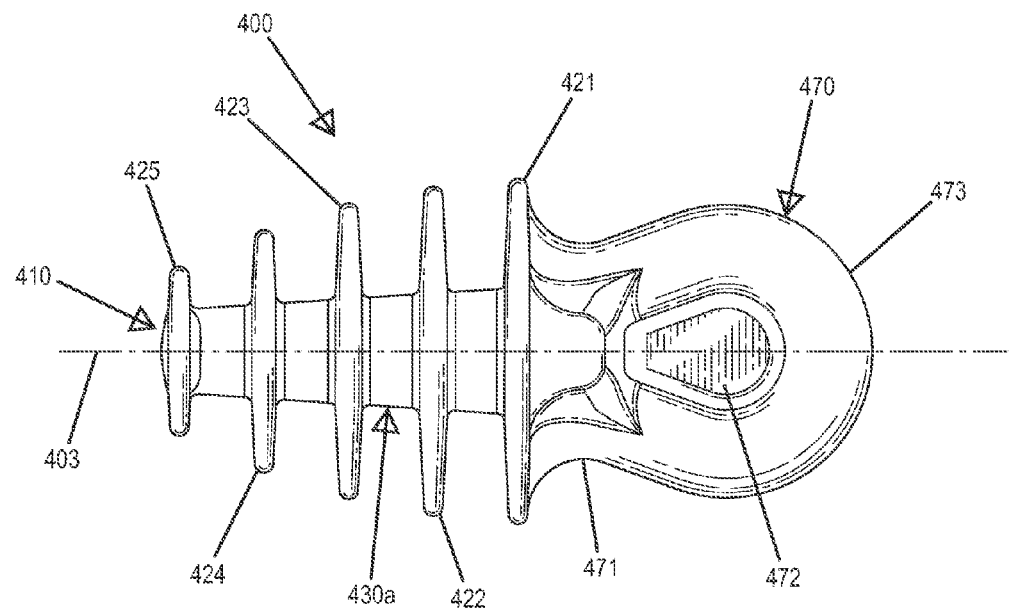
FIG. 4A illustrates a side view of a device for installation in a subject's ear according to a specific example embodiment of the disclosure.
Figure 4B:
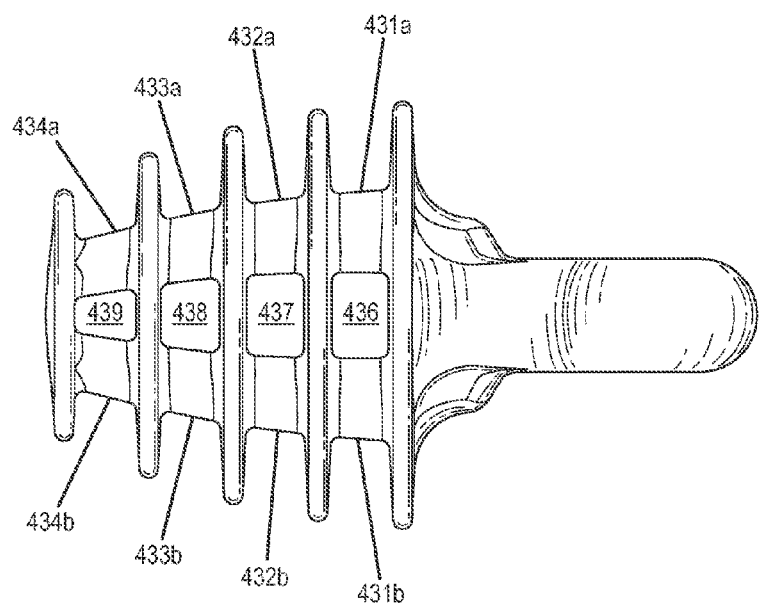
FIG. 4B illustrates a bottom view of a device for installation in a subject's ear according to a specific example embodiment of the disclosure.
Figure 4:
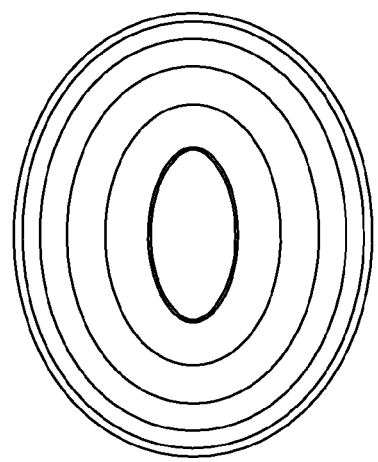
FIG. 4C illustrates a perspective view of a device for installation in a subject's ear according to a specific example embodiment of the disclosure.
FIG. 4D illustrates an end view of a device for installation in a subject's ear according to a specific example embodiment of the disclosure.
Figure 4:
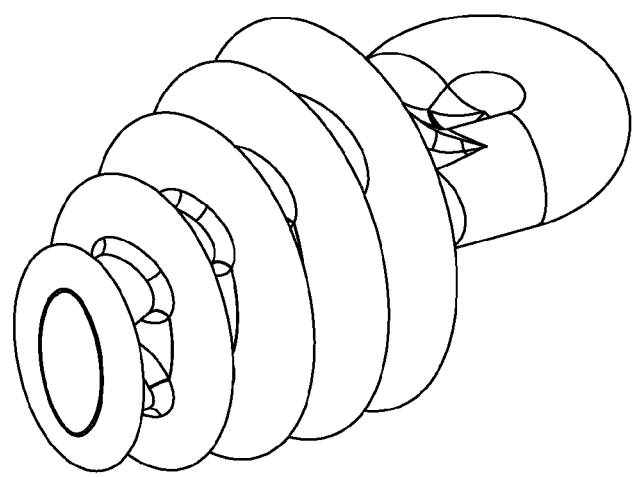

Specific example embodiments of an earpiece are illustrated in FIGS. 3A-3B. Earpiece 300 comprises insert 310 and handle 370 fixed to insert 310. Insert 310 defines longitudinal axis 303 and comprises set of flanges 320 connected along stem 330. Flange set 320 comprises flange 321, flange 322, flange 323, flange 324, and flange 325, wherein flange 321 is the largest and most distal and flange 325 is the smallest and most proximal.

Stem 330 includes stem segments 331, 332, 333, and 334. These segments are defined, at least in part, by flanges 321, 322, 323, 324, and 326 respectively. Stem 330 passes through the centers of generally circular flanges 321, 322, 323, and 324 and tapers from distal (larger) to proximal (smaller) end. Flanges 321, 322, 323, and 324 lie in planes generally perpendicular to axis 303. As shown, segments 331, 332, 333, and 334 may have substantially uniform length. Handle 370 includes generally hourglass-shaped body 373 connected to insert 310 and centered along axis 303. Handle 370 also includes a flattened distal tip.

Specific example embodiments of an earpiece are illustrated in FIGS. 4A-4H. Earpiece 400 comprises insert 410 and handle 470 fixed to insert 410. Insert 410 defines longitudinal axis 403 and comprises set of flanges 420 connected along stems 430a and 430b. Apertures 436, 437, 438, and 439 are flanked by pairs of stem segments 431a, 431b, 432a, 432b, 433a, 422b, 434a, and 434b. Flange set 420 comprises flange 421, flange 422, flange 423, flange 424, and flange 425, wherein flange 421 is the largest and most distal and flange 425 is the smallest and most proximal.

Stem 430a includes stem segments 431a, 432a, 433a, and 434a. Stem 430b includes stem segments 431b, 432b, 433b, and 434b. These segments are defined, at least in part, by flanges 421, 422, 423, 424, and 425 respectively. Stem 430a passes through the upper portion of oblong flanges 421, 422, 423, 424, and 425 and tapers from distal (larger) to proximal (smaller) end. Stems 430a and 430b are also curved towards one another such that apertures 436, 437, 438, and 439 are progressively smaller. Stem 430b passes through the lower portion of oblong flanges 421, 422, 423, 424, and 425 and tapers from distal (larger) to proximal (smaller) end.

As shown, segments segments 431a, 431b, 432a, 432b, 433a, 422b, 434a, and 434b may have substantially uniform length. Flanges 421, 422, 423, 424, and 425 lie in planes generally perpendicular to axis 403.

Handle 470 includes generally disc-shaped body 473 connected via neck 471 to insert 410 and positioned along axis 403. Handle 470 also includes recess 472 positioned generally within the center of disc-shaped body 473. Recess 472 may be contoured to complement a subject's finger tips (e.g., thumb and forefinger). At its proximal end, handle 470 includes a pair of thickenings aligned with stems 430a and 430b.

Figure 5A:
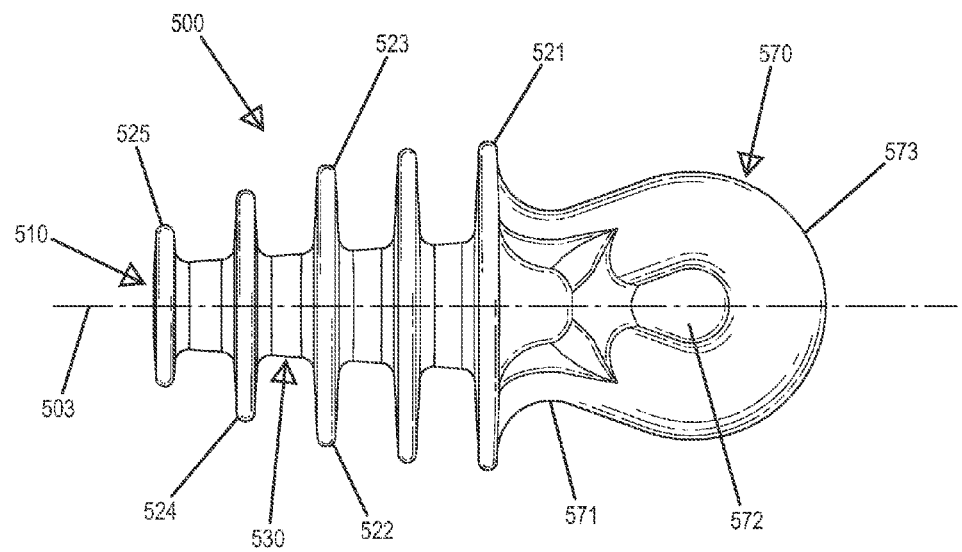
FIG. 5A illustrates a side view of a device for installation in a subject's ear according to a specific example embodiment of the disclosure.
Figure 5B:
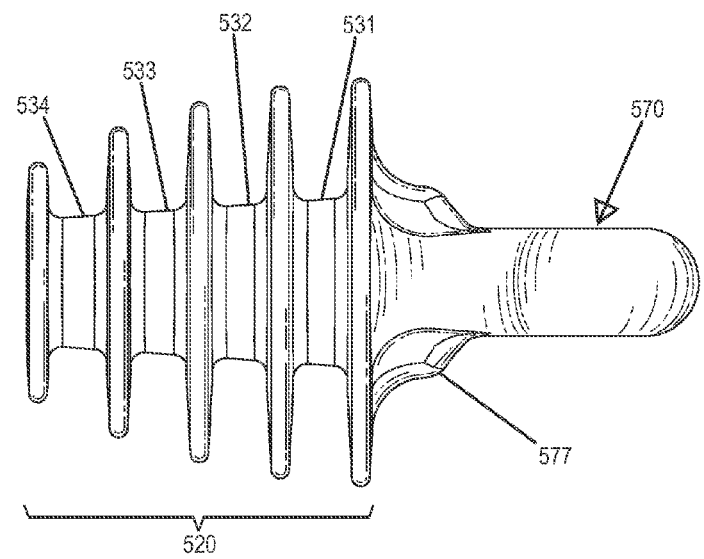
FIG. 5B illustrates a bottom view of a device for installation in a subject's ear according to a specific example embodiment of the disclosure.
Figure 5:
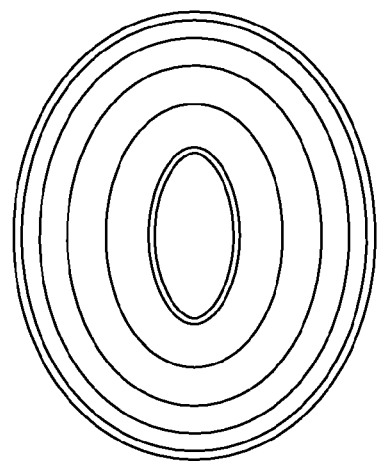
FIG. 5C illustrates a perspective view of a device for installation in a subject's ear according to a specific example embodiment of the disclosure.
FIG. 5D illustrates an end view of a device for installation in a subject's ear according to a specific example embodiment of the disclosure.
Figure 5:
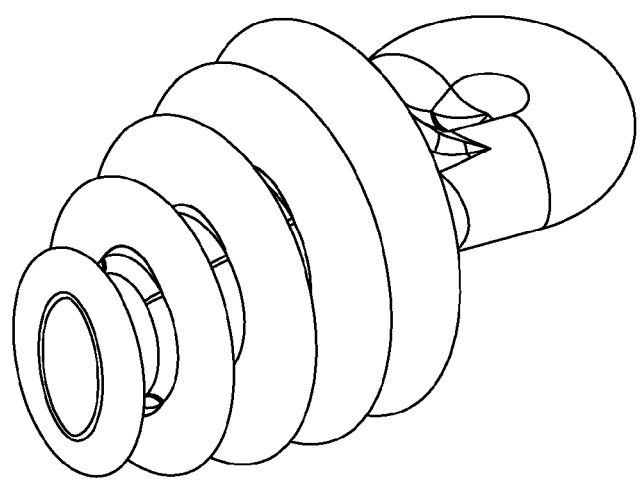

Specific example embodiments of an earpiece are illustrated in FIGS. 5A-5B. Earpiece 500 comprises insert 510 and handle 570 fixed to insert 510. Insert 510 defines longitudinal axis 503 and comprises set of flanges 520 connected along stem 530. Flange set 520 comprises flange 521, flange 522, flange 523, flange 524, and flange 525, wherein flange 521 is the largest and most distal and flange 525 is the smallest and most proximal.

Stem 530 includes stem segments 531, 532, 533, and 534. These segments are defined, at least in part, by flanges 521, 522, 523, 524, and 525 respectively. Stem 530 passes through the centers of oblong flanges 521, 522, 523, and 524 and tapers from distal (larger) to proximal (smaller) end. Flanges 521, 522, 523, and 524 lie in planes generally perpendicular to axis 503. As shown, segments 531, 532, 533, and 534 may have substantially uniform length.

Handle 570 includes generally disc-shaped body 573 connected via neck 571 to insert 510 and positioned along axis 503. Handle 570 also includes recess 572 positioned generally within the center of disc-shaped body 573. Recess 572 may be contoured to complement a subject's finger tips (e.g., thumb and forefinger). At its proximal end, handle 570 includes a pair of thickenings aligned with stem 530.

Figure 6A:
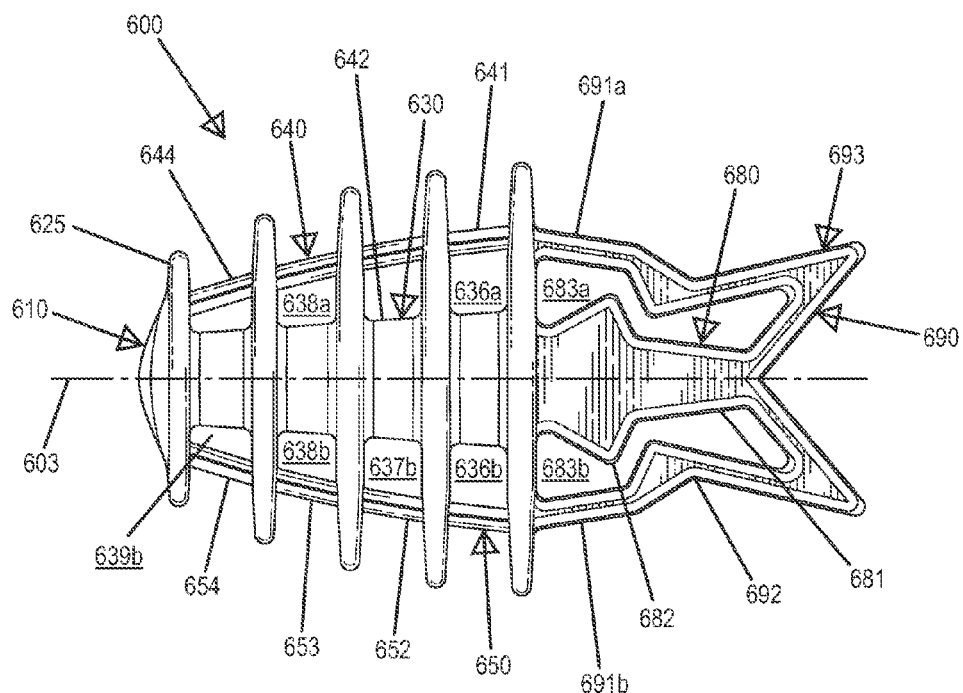
FIG. 6A illustrates a side view of a device for installation in a subject's ear according to a specific example embodiment of the disclosure.
Figure 6B:
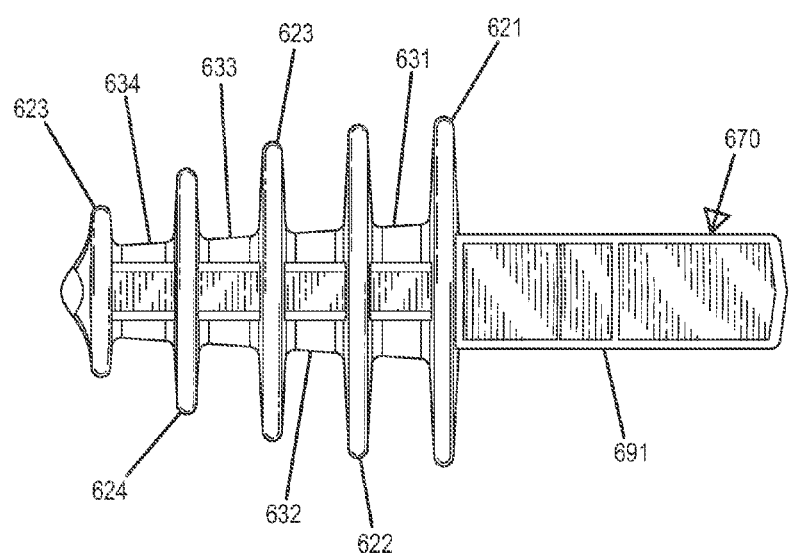
FIG. 6B illustrates a bottom view of a device for installation in a subject's ear according to a specific example embodiment of the disclosure.
Figure 6:
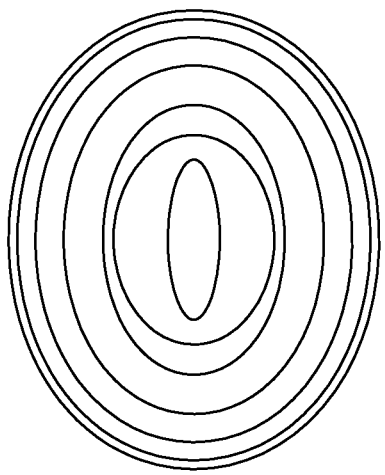
FIG. 6C illustrates a perspective view of a device for installation in a subject's ear according to a specific example embodiment of the disclosure.
FIG. 6D illustrates an end view of a device for installation in a subject's ear according to a specific example embodiment of the disclosure.
Figure 6:
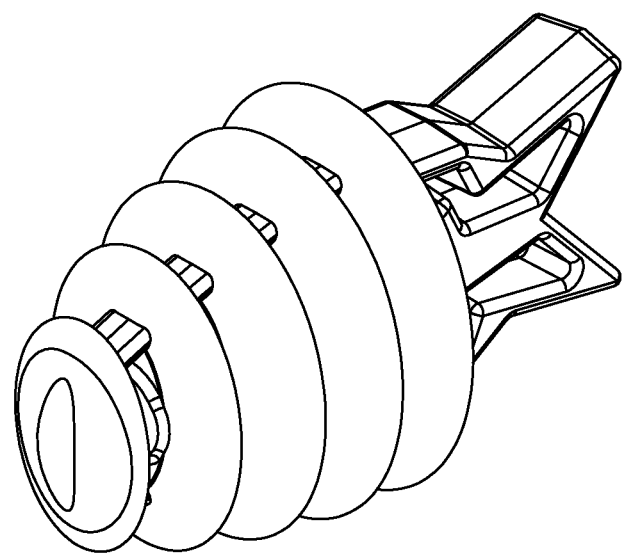

Specific example embodiments of an earpiece are illustrated in FIGS. 6A-6B. Earpiece 600 comprises insert 610 and handle 670 fixed to insert 610. Insert 610 defines longitudinal axis 603 and comprises set of flanges 620 connected along stem 630, stem 640, and frame 650. Flange set 620 comprises flange 621, flange 622, flange 623, flange 624, and flange 625, wherein flange 621 is the largest and most distal and flange 625 is the smallest and most proximal.

Stem 630 includes stem segments 631, 632, 633, and 634. These segments are defined, at least in part, by flanges 621, 622, 623, 624, and 625 respectively. Superior stem 640 includes stem segments 641, 642, 643, and 644. These segments are defined, at least in part, by flanges 621, 622, 623, 624, and 625 respectively. Inferior stem 650 includes stem segments 651, 652, 653, and 654. These segments are defined, at least in part, by flanges 621, 622, 623, 624, and 625 respectively. Stem 630 passes through the centers of oblong flanges 621, 622, 623, 624, and 625 and tapers from distal (larger) to proximal (smaller) end. As shown, segments 631, 632, 633, and 634 may have substantially uniform length. Flanges 621, 622, 623, 624, and 625 lie in planes generally perpendicular to axis 603. Stems 630, 640, and 650 are generally coplanar. Stem segments 631, 632, 633, 634, 641, 642, 643, and 644 along with flanges 621, 622, 623, 624, and 625 define apertures 636a, 637a, 638a, and 639a. Stem segments 631, 632, 633, 634, 651, 652, 653, and 654 along with flanges 621, 622, 623, 624, and 625 define apertures 636b, 637b, 638b, and 639b. Stems 640 and 650 are also curved towards stem 630 such that apertures 636, 637, 638, and 639 are progressively smaller.

Handle 670 comprises stem 680 extending from insert 610 along axis 603. Handle 670 also comprises frame 690 defining the outer periphery of handle 670. Frame 690 includes superior frame member 691a and inferior frame member 691b extending distally from handle 670. As shown, frame members 691a and 691b contact flange 621 opposite of where stems 640 and 650 contact flange 621. Frame members 691a and 691b approach stem 680 at narrowing 692, flare outwardly, and then converge again to meet at stem 680, forming tail 693. Stem 680 comprises body 681 having expansion 682.

Figure 7A:
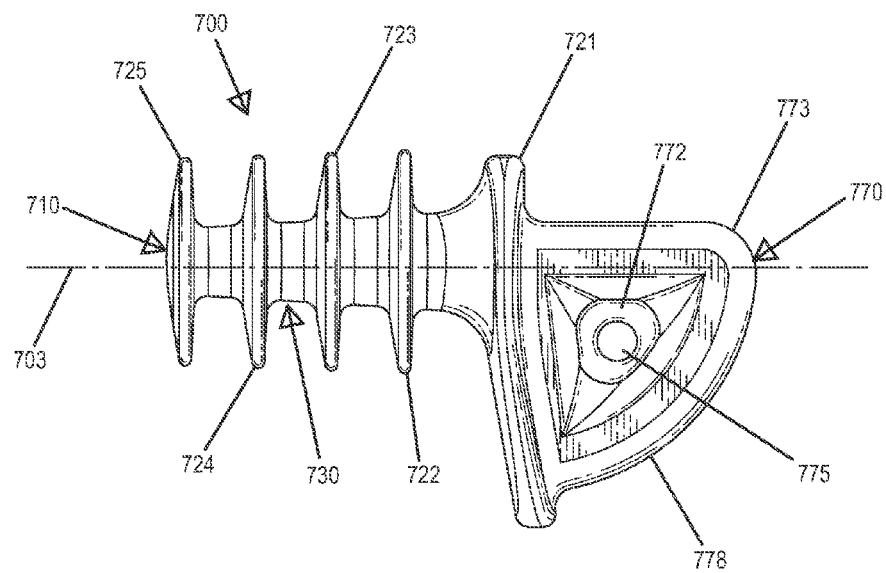
FIG. 7A illustrates a side view of a device for installation in a subject's ear according to a specific example embodiment of the disclosure.
Figure 7B:
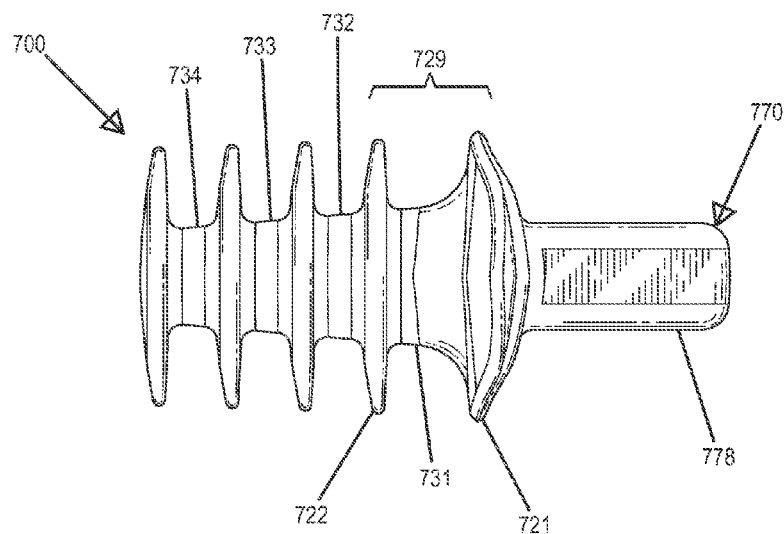
FIG. 7B illustrates a bottom view of a device for installation in a subject's ear according to a specific example embodiment of the disclosure.
Figure 7:
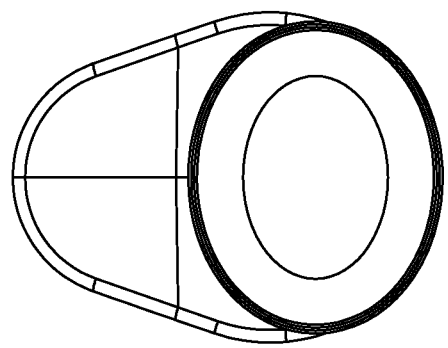
FIG. 7C illustrates a perspective view of a device for installation in a subject's ear according to a specific example embodiment of the disclosure.
FIG. 7D illustrates an end view of a device for installation in a subject's ear according to a specific example embodiment of the disclosure.
Figure 7:
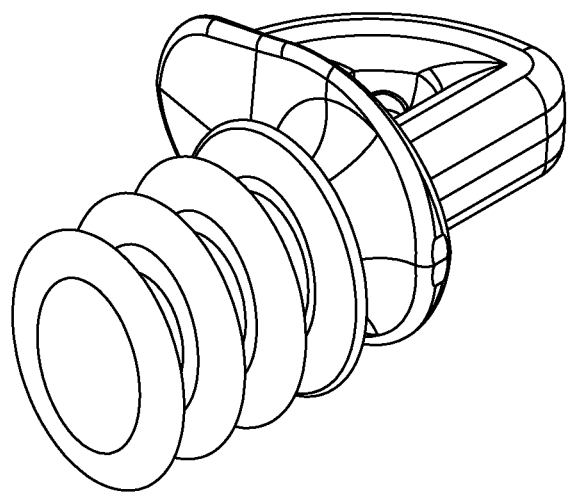

Specific example embodiments of an earpiece are illustrated in FIGS. 7A-7B. Earpiece 700 comprises insert 710 and handle 770 fixed to insert 710. Insert 710 defines longitudinal axis 703 and comprises set of flanges 720 connected along stem 730. Flange set 720 comprises flange 721, flange 722, flange 723, flange 724, and flange 725, wherein flange 721 is the most distal and flange 725 is the most proximal.

Stem 730 has a generally cylindrical shape that lies along longitudinal axis 703. Stem 730 includes stem segments 731, 732, 733, and 734. These segments are defined, at least in part, by flanges 721, 722, 723, 724, and 725 respectively. Stem 730 passes through the centers of oblong flanges 722, 723, and 724 and tapers slightly from distal (larger) to proximal (smaller) end. Flanges 722, 723, and 724 lie in planes generally perpendicular to axis 703. Flange 721 has a central portion that lies in a plane generally perpendicular to axis 703 and an inferior portion that lies in a plane oblique to axis 703. Stem segment 731 is thickened adjacent to the proximal surface of flange 721. As shown, segments 731, 732, 733, and 734 may have substantially uniform length.

Handle 770 is generally triangular-shaped and includes generally cylindrical body 773 extending distally from insert 710 and generally cylindrical support 778 connecting distal end of body 773 to insert 710. The distal surface of flange 721, body 773, and support 778 together form recess 772 and surround and define aperture 775.

Figure 8A:
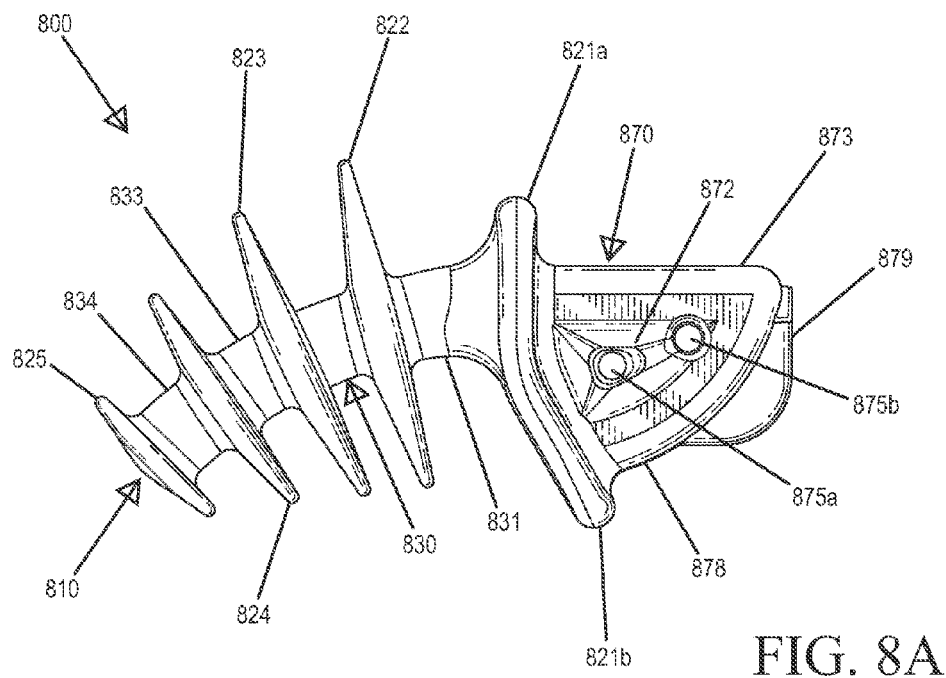
FIG. 8A illustrates a side view of a device for installation in a subject's ear according to a specific example embodiment of the disclosure.
Figure 8B:
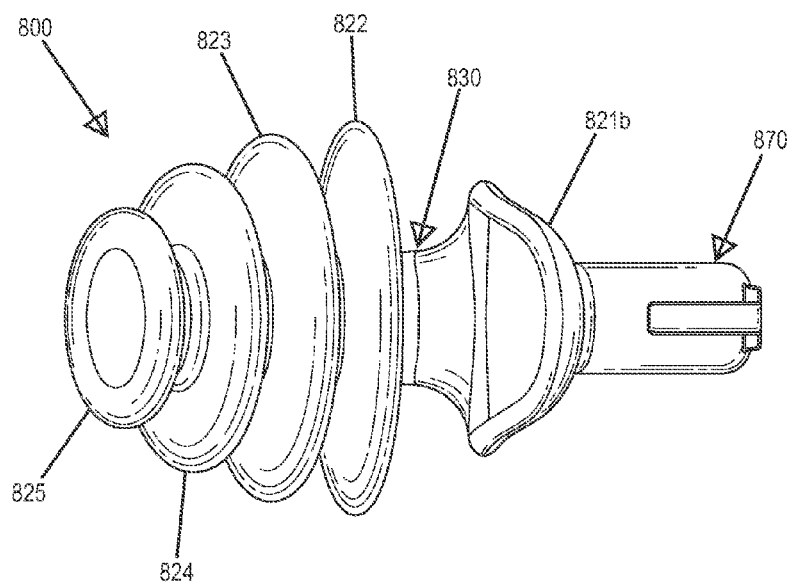
FIG. 8B illustrates a bottom view of a device for installation in a subject's ear according to a specific example embodiment of the disclosure.
Figure 8:
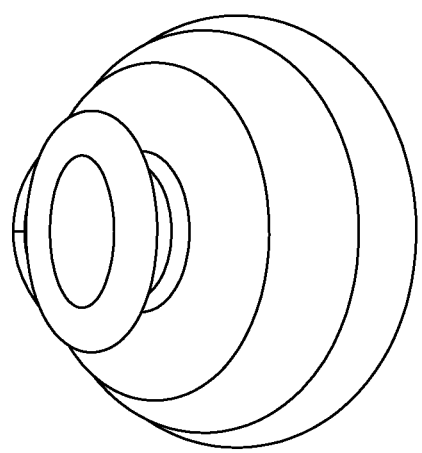
FIG. 8C illustrates a perspective view of a device for installation in a subject's ear according to a specific example embodiment of the disclosure.
FIG. 8D illustrates an end view of a device for installation in a subject's ear according to a specific example embodiment of the disclosure.
Figure 8:
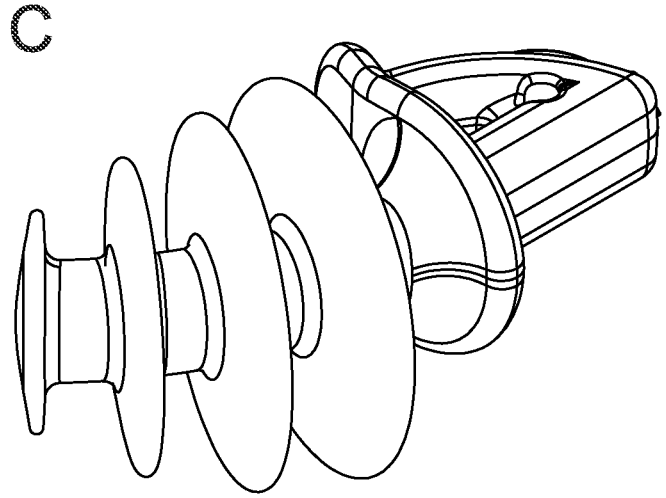

Specific example embodiments of an earpiece are illustrated in FIGS. 8A-8B. Earpiece 800 comprises insert 810 and handle 870 fixed to insert 810. Insert 810 comprises set of flanges 820 connected along stem 830. Flange set 820 comprises flange 821, flange 822, flange 823, flange 824, and flange 825, wherein flange 821 is the most distal and flange 825 is the most proximal.

Stem 830 has a generally tubular shape with an inferiorly biased curvature. Stem 830 includes stem segments 831, 832, 833, and 834. These segments are defined, at least in part, by flanges 821, 822, 823, 824, and 825 respectively. Stem 830 passes through the centers of oblong flanges 822, 823, and 824 and tapers slightly from distal (larger) to proximal (smaller) end. Flanges 822, 823, and 824 lie in planes generally perpendicular to a line tangent to stem 830 at the respective flanges. Flange 821 has a central portion 821a that lies in a plane generally parallel to flange 822 and an inferior portion 821b that lies in a plane oblique to flange 822. Stem segment 831 is thickened adjacent to the proximal surface of flange 821. As shown, segment 931 is about 50% longer than segments 832, 833, and 834, forming flange gap 829. Segments 832, 833, and 834 may have substantially uniform length.

Handle 870 is generally triangular-shaped and includes generally cylindrical body 873 extending distally from insert 810 and generally cylindrical support 878 connecting distal end of body 873 to insert 810. The distal surface of flange 821, body 873, and support 978 together form recess 872 and surround and define apertures 875a and 875b. Handle 870 further comprises protrusion 879 extending distally from support 878 and inferiorly from body 873.

Figure 9A:
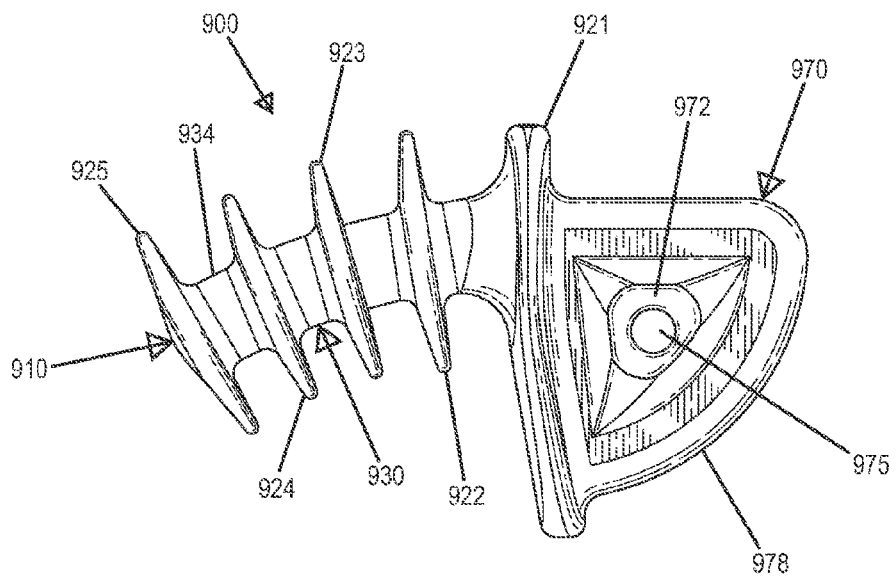
FIG. 9A illustrates a side view of a device for installation in a subject's ear according to a specific example embodiment of the disclosure.
Figure 9B:
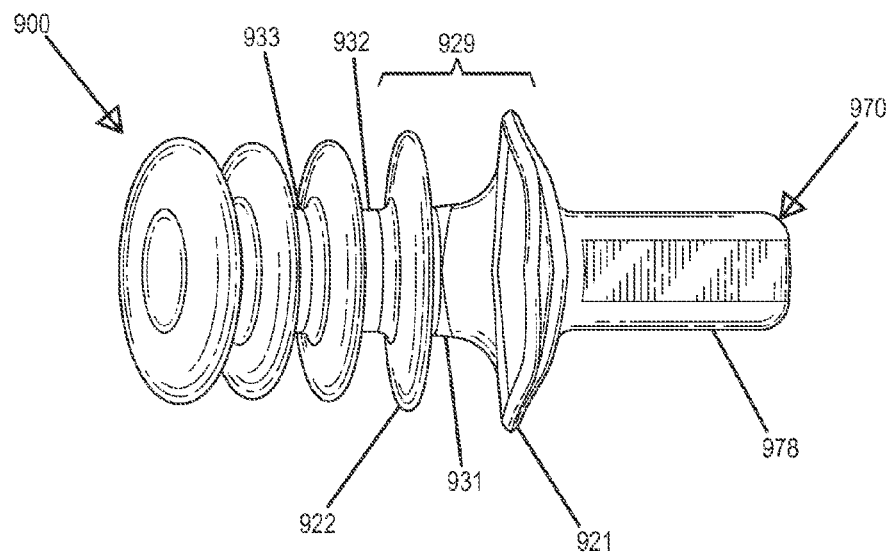
FIG. 9B illustrates a bottom view of a device for installation in a subject's ear according to a specific example embodiment of the disclosure.
Figure 9:
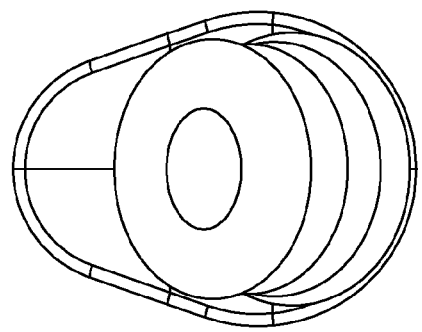
FIG. 9C illustrates a perspective view of a device for installation in a subject's ear according to a specific example embodiment of the disclosure.
FIG. 9D illustrates an end view of a device for installation in a subject's ear according to a specific example embodiment of the disclosure.
Figure 9:
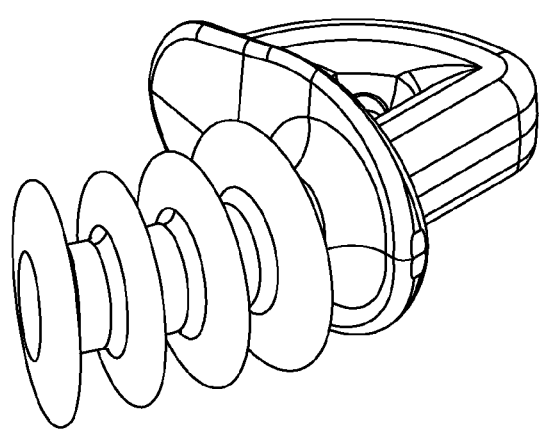

Specific example embodiments of an earpiece are illustrated in FIGS. 9A-9B. Earpiece 900 comprises insert 910 and handle 970 fixed to insert 910. Insert 910 comprises set of flanges 920 connected along stem 930. Flange set 920 comprises flange 921, flange 922, flange 923, flange 924, and flange 925, wherein flange 921 is the most distal and flange 925 is the most proximal.

Stem 930 has a generally tubular shape with an inferiorly biased curvature. Stem 930 includes stem segments 931, 932, 933, and 934. These segments are defined, at least in part, by flanges 921, 922, 923, 924, and 925 respectively. Stem 930 passes through the centers of oblong flanges 922, 923, and 924 and tapers slightly from distal (larger) to proximal (smaller) end. Flanges 922, 923, and 924 lie in planes generally perpendicular to a line tangent to stem 930 at the respective flanges. Flange 921 has a central portion 921a that lies in a plane generally parallel to flange 922 and an inferior portion 921b that lies in a plane oblique to flange 922. Stem segment 931 is thickened adjacent to the proximal surface of flange 921. As shown, segment 931 is about 50% longer than segments 932, 933, and 934, forming flange gap 929. Segments 932, 933, and 934 may have substantially uniform length.

Handle 970 is generally triangular-shaped and includes generally cylindrical body 973 extending distally from insert 910 and generally cylindrical support 978 connecting distal end of body 973 to insert 910. The distal surface of flange 921, body 973, and support 978 together form recess 972 and surround and define aperture 975.

Figure 10A:
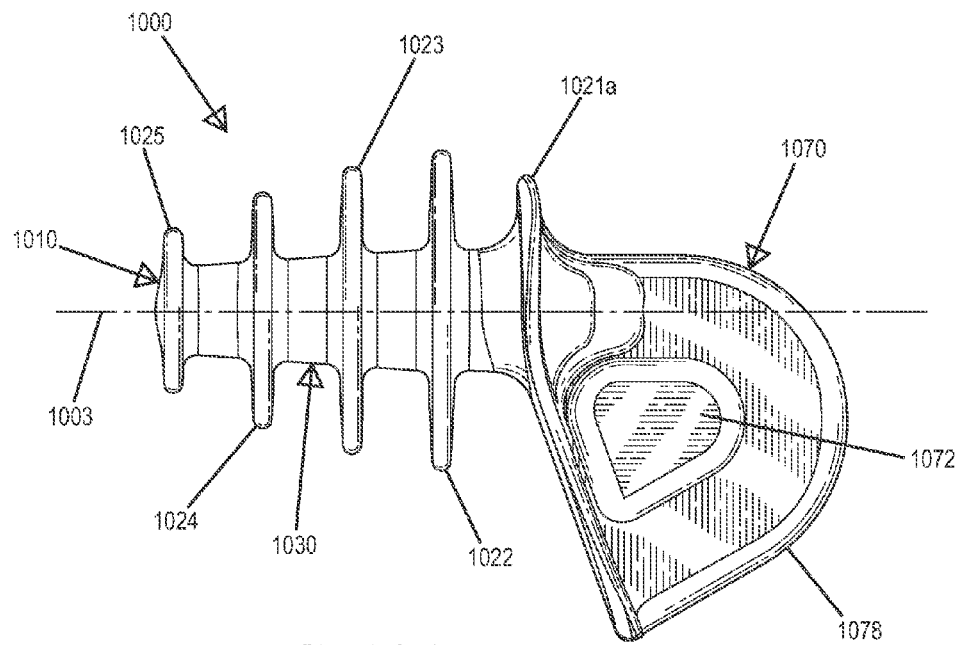
FIG. 10A illustrates a side view of a device for installation in a subject's ear according to a specific example embodiment of the disclosure.
Figure 10B:
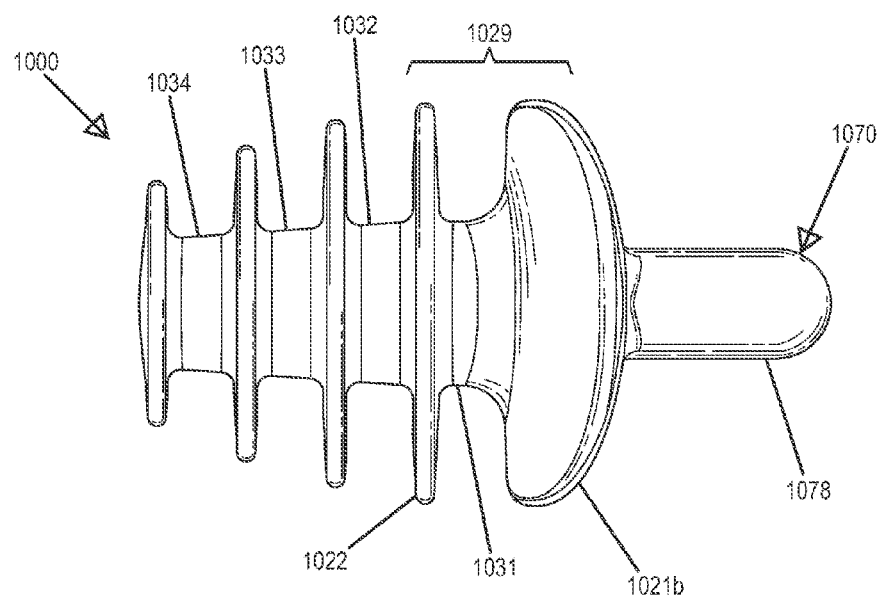
FIG. 10B illustrates a bottom view of a device for installation in a subject's ear according to a specific example embodiment of the disclosure.
Figure 10:
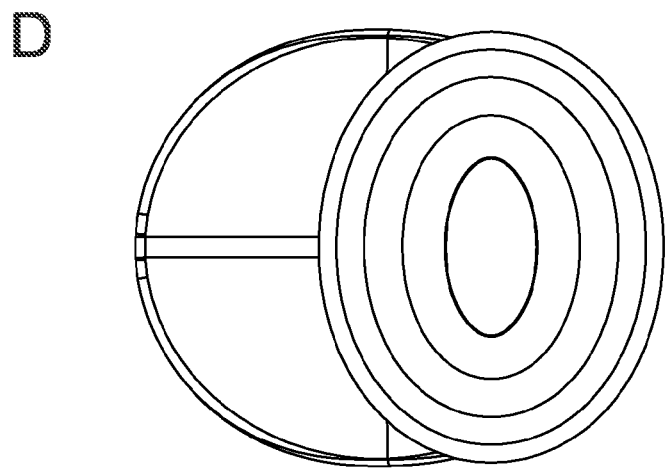
FIG. 10C illustrates a perspective view of a device for installation in a subject's ear according to a specific example embodiment of the disclosure.
FIG. 10D illustrates an end view of a device for installation in a subject's ear according to a specific example embodiment of the disclosure.
Figure 10:
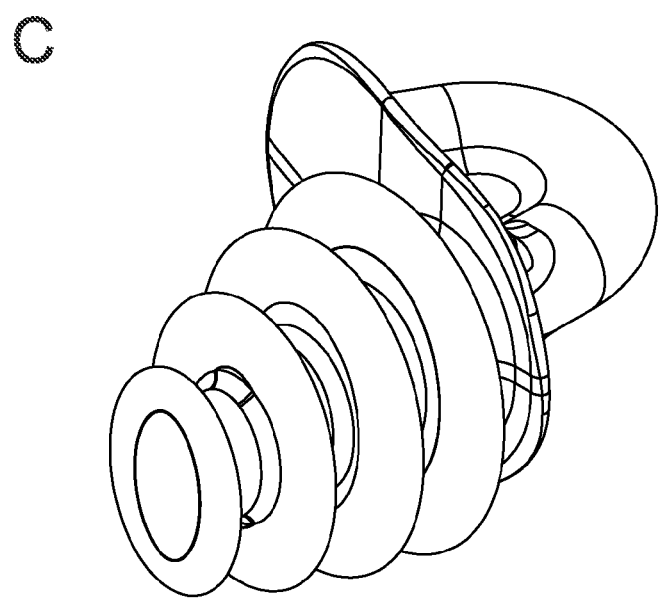

Specific example embodiments of an earpiece are illustrated in FIGS. 10A-10B. Earpiece 1000 comprises insert 1010 and handle 1070 fixed to insert 1010. Insert 1010 defines longitudinal axis 1003 and comprises set of flanges 1020 connected along stem 1030. Flange set 1020 comprises flange 1021, flange 1022, flange 1023, flange 1024, and flange 1025, wherein flange 1021 is the most distal and flange 1025 is the most proximal.

Stem 1030 lies along longitudinal axis 1003 and has an elongated shape with a generally oval cross section. A section of stem 1030 has a generally laterally-oriented major extent generally and a generally vertically-oriented minor extent. Stem 1030 includes stem segments 1031, 1032, 1033, and 1034. These segments are defined, at least in part, by flanges 1021, 1022, 1023, 1024, and 1025 respectively. Stem 1030 passes through the centers of oblong flanges 1022, 1023, and 1024 and tapers slightly from distal (larger) to proximal (smaller) end. Flanges 1022, 1023, and 1024 lie in planes generally perpendicular to axis 1003. Flange 1021 has a central portion 1021a that lies in a plane generally perpendicular to axis 1003 and an inferior portion that lies in a plane oblique to axis 1003. Stem segment 1031 is thickened adjacent to the proximal surface of flange 1021. As shown, segments 1031, 1032, 1033, and 1034 may have substantially uniform length.

Handle 1070 is generally horseshoe-shaped and includes tubular body 1073 extending distally from insert 1010 and curving back to join inferior portion 1021b of flange 1021. The distal surface of flange 1021 and body 1073 together surround and form recess 1072. Recess 1072 may be contoured to complement a subject's finger tips (e.g., thumb and forefinger).

Figure 11A:
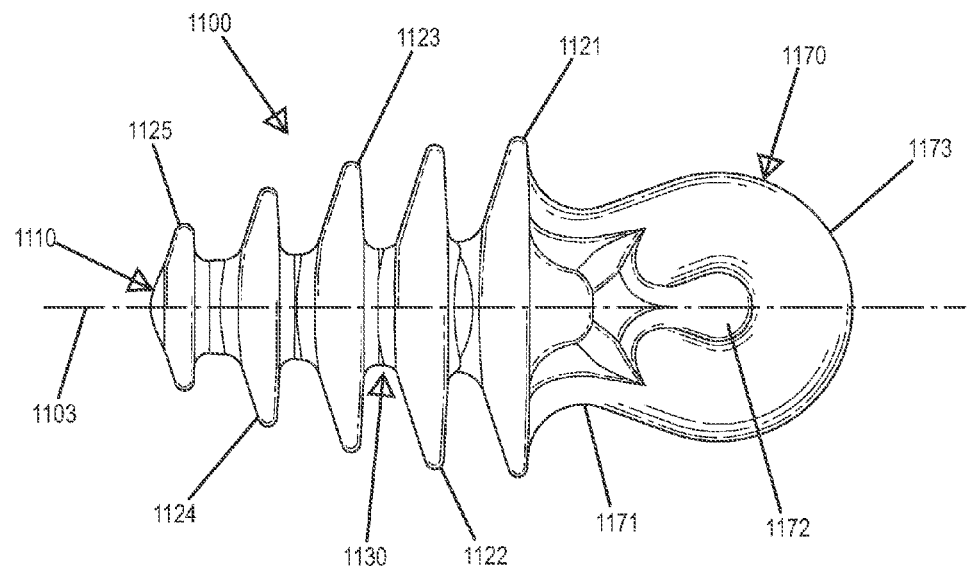
FIG. 11A illustrates a side view of a device for installation in a subject's ear according to a specific example embodiment of the disclosure.
Figure 11B:
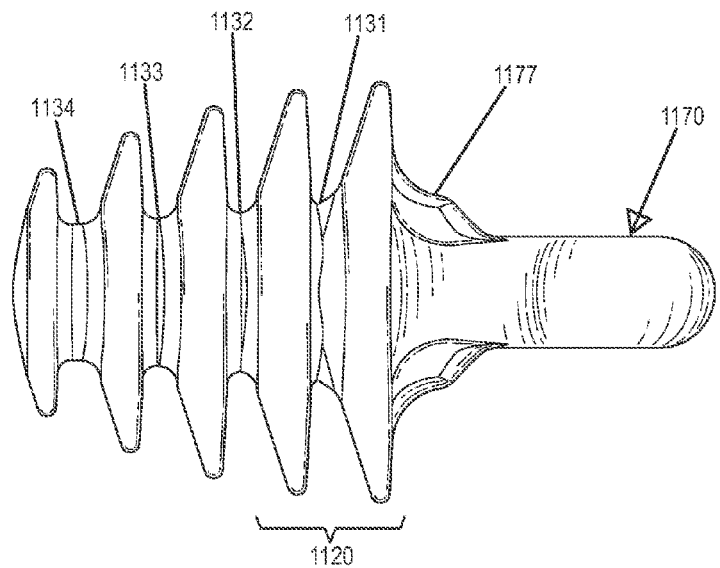
FIG. 11B illustrates a bottom view of a device for installation in a subject's ear according to a specific example embodiment of the disclosure.
Figure 11:
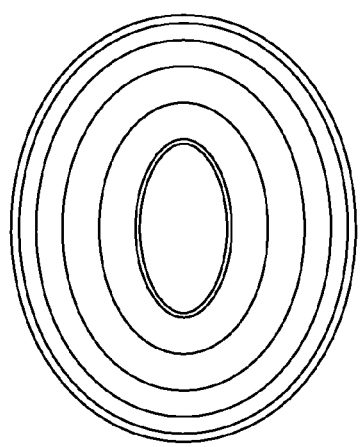
FIG. 11C illustrates a perspective view of a device for installation in a subject's ear according to a specific example embodiment of the disclosure.
FIG. 11D illustrates an end view of a device for installation in a subject's ear according to a specific example embodiment of the disclosure.
Figure 11:
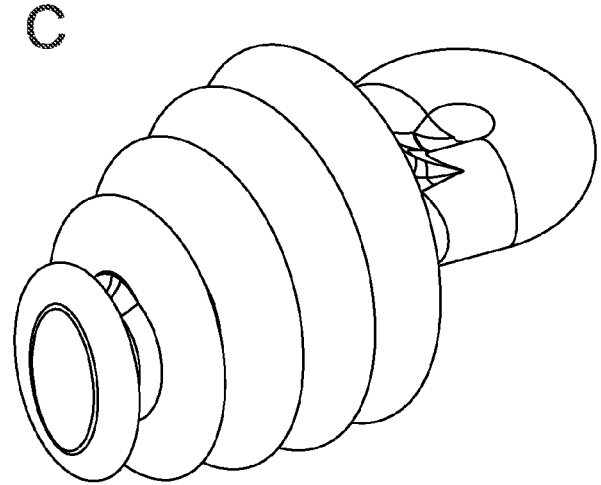

Specific example embodiments of an earpiece are illustrated in FIGS. 11A-11B. Earpiece 1100 comprises insert 1110 and handle 1170 fixed to insert 1110. Insert 1110 defines longitudinal axis 1103 and comprises set of flanges 1120 connected along stem 1130. Flange set 1120 comprises flange 1121, flange 1122, flange 1123, flange 1124, and flange 1125, wherein flange 1121 is the largest and most distal and flange 1125 is the smallest and most proximal.

Stem 1130 lies along longitudinal axis 1103 and has an elongated shape with a generally oval cross section. A section of stem 1130 has a generally laterally-oriented major extent generally and a generally vertically-oriented minor extent. Stem 1130 includes stem segments 1131, 1132, 1133, and 1134. These segments are defined, at least in part, by flanges 1121, 1122, 1123, 1124, and 1125 respectively. Stem 1130 passes through the centers of oblong flanges 1121, 1122, 1123, and 1124 and tapers from distal (larger) to proximal (smaller) end. Flanges 1121, 1122, 1123, and 1124 lie in planes generally perpendicular to axis 1103. As shown, segments 1131, 1132, 1133, and 1134 may have substantially uniform length.

Handle 1170 includes generally disc-shaped body 1173 connected via neck 1171 to insert 1110 and positioned along axis 1103. Handle 1170 also includes recess 1172 positioned generally within the center of disc-shaped body 1173. Recess 1172 may be contoured to complement a subject's finger tips (e.g., thumb and forefinger). At its proximal end, handle 1170 includes a pair of thickenings aligned with stem 1130.

As will be understood by those skilled in the art who have the benefit of the instant disclosure, other equivalent or alternative compositions, devices, methods, and systems for modifying received and/or perceived sound can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the position and number of stems, flanges, apertures, protrusions, recesses, contours may be varied. In some embodiments, inserts and/or handles may be interchangeable. Interchangeability may allow an earpiece's fit and/or manipulability to be custom adjusted (e.g., by interchanging inserts and handles). In addition, the size of a device and/or system may be scaled up (e.g., to be used for adult subjects) or down (e.g., to be used for juvenile subjects) to suit the needs and/or desires of a practitioner. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition, device, and/or system of the disclosure. For example, a composition, device, and/or system may be prepared and or used as appropriate for human use (e.g., with regard to sanitary, infectivity, safety, toxicity, biometric, and other considerations).

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value +/– about 10%, depicted value +/– about 50%, depicted value +/– about 100%) and/or a range endpoint. With respect to the former, a value of 50 depicted in an example, table, and/or drawing may form the basis of a range of, for example, about 45 to about 55, about 25 to about 100, and/or about 0 to about 100.

All or a portion of a device and/or system for modifying received and/or perceived sound may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

EXAMPLES

Some specific example embodiments of the disclosure may be illustrated by one or more of the examples provided herein.

Example 1

Ear Canal Measurements

Ear canal impressions were made from over 100 human ear canals and their dimensions measured. It was observed that the vertical extent was typically larger than the lateral (e.g., generally anterior to posterior) extent. Measurements were taken from these impressions from which it was determined that most subjects have non-circular ear canals with the vertical extent of the impressions ranging from 1.0 to 3.5 times greater than the lateral extent (and not necessarily an axis of symmetry). The curvature of an ear canal and/or the position and direction of the two ear canal bends may impact (e.g., determine) the optimal lengths of the spacings including the important stop gap and the curvature of the stem.

Example 2

Noise Reduction Rating

Tests were performed according to ANSI S3.19-1974 on an earpiece according to an example embodiment of the disclosure as shown in FIGS. 2A-2H. These earpieces were found to have an NRR of 27 in an initial test.

What is claimed is:

1. A device for altering sound received at a subject's ear, the device comprising:
    an elongated earpiece having a proximal portion and a distal portion and defining a longitudinal axis, wherein the proximal portion comprises:
        an insert configured for at least partial insertion in the canal of the subject's ear,
        the insert comprising:
            a first elongated stem positioned generally parallel to the longitudinal axis and tapering from its distal end to its proximal end;
            at least 3 insert flanges, each insert flange fixed along the length of the stem generally perpendicular to the longitudinal axis; and
            a stop flange fixed to the stem distal to the insert flanges at its distal end and having an outer periphery with a major extent and a minor extent with the major extent greater than the minor extent, and
        the distal portion comprises:
            a handle fixed to at least a portion of a distal surface of the stop flange and configured to guide insertion of the insert in the subject's ear canal.

2. A device according to claim 1, wherein each insert flange has an outer periphery that is independently selected from the group consisting of generally circular, generally oval, generally elliptical, generally lunar, and asymmetric.

3. A device according to claim 1, wherein each insert flange is generally planar with a major axis and a minor axis; and dimensioned to have an extent along its major axis that is about 1× to about 4× its extent along its minor axis.

4. A device according to claim 1, wherein the stop flange has an oblong outer periphery that is independently selected from the group consisting of generally oval, generally elliptical, generally lunar, and asymmetric.

5. A device according to claim 1, wherein the stop flange is generally planar with a major axis and a minor axis; and dimensioned to have an extent along its major axis that is about 1× to about 4× its extent along its minor axis.

6. A device according to claim 1, wherein the at least 3 insert flanges, each insert flange fixed along the length of the stem generally perpendicular to the longitudinal axis further comprises each insert flange fixed generally at its center to the stem.

7. A device according to claim 1, wherein the insert flanges vary in size with the smallest having the most proximal stem position.

8. A device according to claim 7, wherein the largest insert flange has the most distal stem position.

9. A device according to claim 1, wherein the stem curves away from the longitudinal axis at its proximal end.

10. A device according to claim 1, wherein the insert further comprises:
    a second elongated stem positioned generally parallel to the longitudinal axis and tapering from its distal end to its proximal end, wherein each insert flange is fixed along the length of the second stem generally perpendicular to the longitudinal axis.

11. A device according to claim 10 further comprising an aperture along the longitudinal axis, the aperture at least partially defined by the first stem and the second stem.

12. A device according to claim 10, wherein the insert further comprises:
 a third elongated stem positioned generally parallel to the longitudinal axis and tapering from its distal end to its proximal end,
 wherein each insert flange is fixed along the length of the third stem generally perpendicular to the longitudinal axis.

13. A device according to claim 12 further comprising an aperture along the longitudinal axis, the aperture at least partially defined by the first stem, the second stem, and the third stem.

14. A device according to claim 1, wherein the at least 3 insert flanges are evenly spaced apart from each other and from the stop flange.

15. A device according to claim 1, wherein the at least 3 insert flanges are spaced apart from each other along the stem by a first distance ($d_1$) and the most distal insert flange is spaced apart from the stop flange by a second distance ($d_2$), wherein the first distance ($d_1$) is about 25% to about 100% of the second distance ($d_2$).

16. A device according to claim 1, wherein the handle further comprises a generally cylindrically shaped body, a generally ovally shaped body, a generally triangularly shaped body, a generally fish-tail shaped body, and an asymmetric body.

17. A device according to claim 1, wherein the handle further comprises a generally planar body having a first lateral surface and a second lateral surface.

18. A device according to claim 17, wherein the first lateral surface comprises a first lateral recess configured to contact a human finger and the second lateral surface comprises a second lateral recess configured to contact a human thumb.

19. A device according to claim 17, wherein the handle further comprises at least one through hole from the first lateral surface to the second lateral surface.

20. A device according to claim 1, wherein the handle further comprises a generally cylindrical body extending distally from the insert and a support having a first end fixed to the distal end of the body and a second end fixed to at least a portion of a distal surface of the stop flange.

21. A device according to claim 20, wherein the body, the stop flange and the support have a generally triangular periphery and define a first lateral surface comprising a first lateral recess and a second lateral surface comprising a second lateral recess.

22. A device according to claim 21, wherein the handle further comprises a through hole from the first lateral surface to the second lateral surface.

23. A device according to claim 1, wherein the stop flange is thicker than the insert flanges.

* * * * *